(12) United States Patent
Barnes et al.

(10) Patent No.: US 12,098,152 B2
(45) Date of Patent: Sep. 24, 2024

(54) METHODS AND COMPOSITIONS FOR TREATING POLYCYSTIC OVARY SYNDROME

(71) Applicant: Spruce Biosciences, Inc., South San Francisco, CA (US)

(72) Inventors: Christopher Barnes, South San Francisco, CA (US); David Karpf, South San Francisco, CA (US); Mustafa Noor, South San Francisco, CA (US)

(73) Assignee: SPRUCE BIOSCIENCES, INC., South San Francisco, CA (US)

( * ) Notice: Subject to any disclaimer, the term of this patent is extended or adjusted under 35 U.S.C. 154(b) by 0 days.

(21) Appl. No.: 18/107,979

(22) Filed: Feb. 9, 2023

(65) Prior Publication Data

US 2023/0295161 A1    Sep. 21, 2023

Related U.S. Application Data

(63) Continuation of application No. PCT/US2021/045780, filed on Aug. 12, 2021.

(60) Provisional application No. 63/064,863, filed on Aug. 12, 2020.

(51) Int. Cl.
*C07D 471/04* (2006.01)
*A61P 15/08* (2006.01)

(52) U.S. Cl.
CPC ............ *C07D 471/04* (2013.01); *A61P 15/08* (2018.01)

(58) Field of Classification Search
CPC .................................................. C07D 471/04
USPC ...................................................... 514/259.1
See application file for complete search history.

(56) References Cited

U.S. PATENT DOCUMENTS

| | | | |
|---|---|---|---|
| 5,356,897 A | 10/1994 | Oku et al. | |
| 8,030,304 B2 * | 10/2011 | Chen ................... | A61P 13/12 514/366 |
| 8,563,718 B2 * | 10/2013 | Rizzo ................... | A61P 25/00 544/281 |
| 10,849,908 B2 | 12/2020 | Howerton et al. | |
| 11,007,201 B2 | 5/2021 | Howerton et al. | |
| 11,311,549 B2 | 4/2022 | Howerton et al. | |
| 11,344,557 B2 | 5/2022 | Howerton et al. | |
| 11,351,177 B2 | 6/2022 | Howerton et al. | |
| 11,708,372 B2 | 7/2023 | Reddy et al. | |
| 2002/0013357 A1 | 1/2002 | Nadkarni et al. | |
| 2003/0008885 A1 | 1/2003 | He et al. | |
| 2003/0092602 A1 | 5/2003 | Leach et al. | |
| 2005/0209250 A1 | 9/2005 | Romano | |
| 2006/0078623 A1 | 4/2006 | Dhoot et al. | |
| 2008/0161235 A1 | 7/2008 | Chen et al. | |
| 2008/0269279 A1 | 10/2008 | Clements et al. | |
| 2009/0076266 A1 | 3/2009 | Daugulis et al. | |
| 2010/0022560 A1 | 1/2010 | Chen et al. | |
| 2010/0155595 A1 | 6/2010 | Ghoshal et al. | |
| 2010/0166889 A1 | 7/2010 | Sanfilippo | |
| 2010/0222339 A1 | 9/2010 | Chen et al. | |
| 2011/0136865 A1 | 6/2011 | Buntinx | |
| 2011/0166345 A1 | 7/2011 | Rizzo et al. | |
| 2013/0045079 A1 | 2/2013 | Sanfilippo | |
| 2017/0020877 A1 | 1/2017 | Grigoriadis | |
| 2017/0333126 A1 | 11/2017 | Sobotka | |
| 2018/0110554 A1 | 4/2018 | Zarins et al. | |
| 2019/0262349 A1 | 8/2019 | Howerton et al. | |
| 2020/0255436 A1 * | 8/2020 | Howerton ............... | A61K 9/20 |
| 2021/0015827 A1 | 1/2021 | Howerton et al. | |
| 2021/0038604 A1 | 2/2021 | Howerton et al. | |
| 2021/0137935 A1 | 5/2021 | Howerton et al. | |
| 2021/0322430 A1 | 10/2021 | Howerton et al. | |
| 2021/0361664 A1 | 11/2021 | Howerton et al. | |
| 2022/0133742 A1 | 5/2022 | Ghosh et al. | |
| 2022/0143037 A1 | 5/2022 | Howerton et al. | |
| 2023/0322775 A1 | 10/2023 | Barnes et al. | |
| 2024/0043432 A1 | 2/2024 | Reddy et al. | |

FOREIGN PATENT DOCUMENTS

| | | |
|---|---|---|
| CN | 1157620 A | 8/1997 |
| CN | 1665792 A | 9/2005 |
| CN | 101516887 A | 8/2009 |
| CN | 101600427 A | 12/2009 |
| CN | 101880276 A | 11/2010 |
| CN | 106102740 A | 11/2016 |
| CN | 107635474 A | 1/2018 |
| CN | 107635557 A | 1/2018 |
| EP | 2094709 B1 | 9/2010 |

(Continued)

OTHER PUBLICATIONS

Asakura et al., Journal of Clinical Endocrinology and Metabolism, vol. 82, No. 8, pp. 2720-2725.*
EP20844541.1 Extended European Search Report dated May 31, 2023.
Sarafoglou et al. SUN-LB064 A Phase 2, Dose-Escalation, Safety and Efficacy Study of Tildacerfont (SPR001) for the Treatment of Patients with Classic Congenital Adrenal Hyperplasia. Journal of the Endocrine Society. 2017. vol. 3, Supplement No. 1.
Spruce Biosciences, Inc. Study of SPR001 in Adults with Classic Congenital Adrenal Hyperplasia. 2017. pp. 1-7. Spruce Biosciences, Inc. Study to Evaluate the Safety and Efficacy of SPR001 in Subjects with Classic Congenital Adrenal Hyperplasia. 2018. pp. 1-7.

(Continued)

*Primary Examiner* — Niloofar Rahmani
(74) *Attorney, Agent, or Firm* — WILSON SONSINI GOODRICH & ROSATI

(57) ABSTRACT

Polycystic ovary syndrome (PCOS) is characterized by elevated levels of androgens, cysts in the ovaries, and irregular periods. Women with PCOS present with additional symptoms, including hirsutism, alopecia, acne, infertility, weight gain, fatigue, depression and mood changes. The present disclosure provides new compounds, salts, compositions and uses thereof in the treatment of PCOS due to elevated adrenal androgens. Further, the present disclosure provides methods for treating PCOS due to elevated adrenal androgens.

21 Claims, No Drawings

(56) References Cited

FOREIGN PATENT DOCUMENTS

| | | | |
|---|---|---|---|
| EP | 3784233 A1 | 3/2021 | |
| EP | 3984523 A1 | 4/2022 | |
| JP | 2000503661 A | 3/2000 | |
| JP | 2000302693 A | 10/2000 | |
| JP | 2002501922 A | 1/2002 | |
| JP | 2002513382 A | 5/2002 | |
| JP | 2008533201 A | 8/2008 | |
| JP | 2010504344 A | 2/2010 | |
| JP | 2012504626 A | 2/2012 | |
| JP | 2017503030 A | 1/2017 | |
| JP | 2018510012 A | 4/2018 | |
| KR | 19990067391 A | 8/1999 | |
| KR | 20090052366 A | 5/2009 | |
| WO | WO-9413676 A1 | 6/1994 | |
| WO | WO-9729109 A1 | 8/1997 | |
| WO | WO-9803510 A1 | 1/1998 | |
| WO | WO-9808847 A1 | 3/1998 | |
| WO | WO-0059908 A2 | 10/2000 | |
| WO | WO-0123388 A2 | 4/2001 | |
| WO | WO-02072202 A1 | 9/2002 | |
| WO | WO-2005020910 A2 | 3/2005 | |
| WO | WO-2005063755 A1 | 7/2005 | |
| WO | WO-2005079868 A2 | 9/2005 | |
| WO | WO-2006102194 A1 | 9/2006 | |
| WO | WO-2007090087 A2 | 8/2007 | |
| WO | WO-2008036579 A1 | 3/2008 | |
| WO | WO-2010039678 A1 | 4/2010 | |
| WO | WO-2013160317 A2 | 10/2013 | |
| WO | WO-2015112642 A1 | 7/2015 | |
| WO | 2019036503 | * | 2/2019 |
| WO | WO-2019036472 A1 | 2/2019 | |
| WO | WO-2019036503 A1 | 2/2019 | |
| WO | 2019210266 | * | 10/2019 |
| WO | WO-2019210266 A1 | 10/2019 | |
| WO | 2021016208 | * | 1/2021 |
| WO | WO-2022036123 A1 | 2/2022 | |
| WO | WO-2023091684 A1 | 5/2023 | |

OTHER PUBLICATIONS

U.S. Appl. No. 18/209,405 Notice of Allowance dated Aug. 17, 2023.

Co-pending U.S. Appl. No. 18/307,718, inventor Howerton; Alexis, filed Apr. 26, 2023.

Co-pending U.S. Appl. No. 18/310,463, inventor Reddy; Dasharatha, filed May 1, 2023.

PCT/US2020/042820 International Search Report and Written Opinion dated Nov. 25, 2020.

U.S. Appl. No. 16/639,540 Office Action dated May 25, 2023.

U.S. Appl. No. 17/720,074 Notice of Allowance dated Mar. 28, 2023.

Zasadny, Will. Spruce Biosciences Raises $88 Million in Series B Financing, co-led by Omega Funds and Abingworth. Feb. 19, 2020. Business Wire.

Bornstein et al. Diagnosis and Treatment of Primary Adrenal Insufficiency: An Endocrine Society Clinical Practice Guideline. J Clin Endocrinol Metab 101(2):364-389 (2016).

Chen et al. Design of 2,5-Dimethyl-3-(6-dimethyl-4-methylpyridin-3-yl)-7-dipropyl aminopryazolo[1,5-a]pyrimidine (NBI 30775/R121919) and Structure-Activity Relationships of a Series of Potent and Orally Active Corticotropin—Releasing Factor Receptor Antagonists. J. O Medicinal Chemistry Society 47(19) 4787-4798 XP001206057 (2004).

Co-pending U.S. Appl. No. 17/720,074, inventors Reddy; Dasharatha et al., filed Apr. 13, 2022.

Co-pending U.S. Appl. No. 18/078,649, inventors Howerton; Alexis et al., filed Dec. 9, 2022.

Dave. Overview of pharmaceutical excipients used in tablets and capsules. https://www.drugtopics.com/view/overview-pharmaceutical-excipients-used-tablets-and-capsules (Oct. 24, 2008).

EP18846043.0 Extended Search Report dated Feb. 10, 2021.

EP18846689.0 Extended European Search Report dated Dec. 22, 2020.

Escobar-Morreale, HF., Polycystic ovary syndrome: definition, aetiology, diagnosis and treatment. Nat Rev Endocrinol. 14(5):270-284 (2018).

Fuqua et al. Duration of suppression of adrenal steroids after glucocorticoid administration. Int J Pediatr Endocrinol 2010:712549 (2010).

Gehlert et al. 3-(4-Chloro-2-morpholin-4-yl-thiazol-5-yl )-8-(1-ethylpropyl)-2,6-dimethyl-imidazo[I,2-b]pyridazine: a novel brain-penetrant, orally available corticotropin-releasing factor receptor 1 antagonist with efficacy in animal models of alcoholism. The Journal of Neuroscience 27(10):2718-2726 (2007).

Gennaro. Remington: The Science and Practice of Pharmacy. 21st Ed. Mack Pub. Co., Easton, PA (2005).

Gilligan P. et al., The Discovery of 4-(3-Pentylamino)-2,7-dimethyl-8-(2-methyl-4-methoxyphenyl)-pyrazolo-[1,5-alpha]-pyrimidine: A corticotrophin-Releasing Factor (hCRF1)Antagonist. Bioorganic & Medicinal Chemistry 181-189 (2000).

He Liqi et al. 4-(1,3-Dimethoxyprop-2-ylamino)-2,7-dimethyl-8-(2,4-dichlorophenyl)pyrazolo[1,5-a]-1,3,5-triazine: A Potent, Orally Bioavailable CRF1 Receptor Antagonist. J. Of Medicinal Chem. American Chem. Society. Washington, US, vol. 43, 449-456 XP002196777 (2000).

Hien-Quang Do. A General Method for Copper-Catalyzed Arylation of Arene C—H Bonds. J Am Chem Soc. Nov. 12, 2008; 130(45): 15185-15192.

Hien-Quang Do. Copper-Catalyzed Arylation and Alkenylation of Polyfluoroarene C—H Bonds. Journal of American Chemical Society 2008, 1128-1129.

Hien-Quang Do. Copper-Catalyzed Arylation of Heterocycle C—H Bonds. J Am Chem Soc. Oct. 17, 2007; 129(41): 12404-12405.

Hodgetts et al. Discovery of N-(1-ethylpropyl)-[3-methoxy-5-(2-methoxy-4-trifluoromethoxyphenyl)-6-methyl-pyrazin-2-yl]amine 59 (NGD 98-2): an orally active corticotropin releasing factor-1 (CRF-1) receptor antagonist. J Med Chem 54:4187-4206 (2011).

Khadilkar et al., Can polycystic ovarian syndrome be cured? Unfolding the concept of secondary polycystic ovarian syndrome. J Obstet Gynaecol India 69(4):297-302 (2019).

Lee et al. Attenuated Forms of Congenital Adrenal Hyperplasia due to 21-Hydroxylase Deficiency. J Clin Endocrinol Metab. 55(5):866-871 (1982).

Majo et al. Facile Palladium-Catalyzed Synthesis of 3-Arylpyrazolo-[1,5-a]pyrimidines. Adv. Synth. Catal. 2003, 620-624.

Malvern Instruments Worldwide. A Basic Guide to Particle Characterization. Inform—White Paper. 2012. 26 Pages.

O'Reilly et al., 11-oxygenated C19 steroids are the predominant androgens in polycystic ovary syndrome. J Clin Endocrinol Metab. 102(3):840-848 (2017).

PCT/US2007/078605 Written Opinion dated Mar. 20, 2009.

PCT/US2009/058722 International Search Report dated Apr. 8, 2010.

PCT/US2009/058722 Written Opinion dated Apr. 2, 2011.

PCT/US2018/046707 International Search Report and Written Opinion dated Oct. 24, 2018.

PCT/US2018/046760 International Search Report and Written Opinion dated Oct. 24, 2018.

PCT/US2021/045780 International Search Report and Written Opinion dated Dec. 17, 2021.

PCT/US2022/050436 International Search Report and Written Opinion dated Nov. 18, 2022.

Rosenfield et al., The pathogenesis of polycystic ovary syndrome (PCOS): the hypothesis of PCOS as functional ovarian hyperandrogenism revisited. Endocrine Reviews 37(5):467-520 (2016).

Sarafoglou et al. Tildacerfont in Adults with Classic Congenital Adrenal Hyperplasia: Results from Two Phase 2 Studies. J Clin Endocrinol Metab. Oct. 21, 2021; 106(11):e4666-e4679.

Thakral et al. Salt Disproportionation in the Solid State: Role of Solubility and Counterion Volatility. Mol Pharm 13(12):4141-4151 (2016).

Turcu et al. Single-Dose Study of a Corticotripin-Releasing Factor Receptor-1 Antagonist in Women With 21-Hydroxylase Deficiency. J Clin Endocrinol Metab 101(3):1174-1180 (2016).

(56) References Cited

OTHER PUBLICATIONS

U.S. Appl. No. 16/388,620 Notice of Allowance dated Sep. 30, 2020.
U.S. Appl. No. 17/063,592 Notice of Allowance dated Mar. 25, 2022.
U.S. Appl. No. 17/078,054 Notice of Allowance dated Mar. 9, 2021.
U.S. Appl. No. 17/359,414 Notice of Allowance dated Mar. 4, 2022.
U.S. Appl. No. 17/586,228 Office Action dated Jun. 10, 2022.
U.S. Appl. No. 12/377,733 Notice of Allowance dated May 27, 2011.
U.S. Appl. No. 16/388,620 Office Action dated Jul. 15, 2019.
U.S. Appl. No. 16/388,620 Office Action dated Nov. 25, 2019.
U.S. Appl. No. 16/639,540 Office Action dated Jul. 11, 2022.
U.S. Appl. No. 16/639,540 Office Action dated Nov. 16, 2021.
U.S. Appl. No. 17/063,592 Office Action dated Dec. 7, 2021.
U.S. Appl. No. 17/078,054 Office Action dated Dec. 14, 2020.
U.S. Appl. No. 17/359,411 Notice of Allowance dated Apr. 28, 2022.
U.S. Appl. No. 17/359,411 Notice of Allowance dated Apr. 4, 2022.
U.S. Appl. No. 17/359,411 Notice of Allowance dated Mar. 22, 2022.
U.S. Appl. No. 17/359,411 Office Action dated Jan. 6, 2022.
U.S. Appl. No. 17/359,414 Office Action dated Nov. 16, 2021.
U.S. Appl. No. 17/720,074 Office Action dated Aug. 26, 2022.
Varma. Excipients used in the Formulation of Tablets. https://www.rroij.com/openaccess/excipients-used-in-the-formulationof-tablets-.php?aid=78260 Revised date: Jul. 26, 2016.
Zhang et al. D-Level Essay in Statistics, 2009, How to Analyze Change from Baseline. Available at http://www.statistics.du.se/essays/D09 Zhang%20Ling%20&%20Han%20Kun.pdf (Jun. 10, 2009).
Abcam. CP 154526 hydrochloride, non-peptide CRF1 receptor antagonist ab141429. Product datasheet. Retrieved online on Sep. 19, 2023 at: https://www.abcam.com/products/biochemicals/cp-154526-hydrochloride-non-peptide-crf1-receptor-antagonist-ab141429.html. 2 pages.
Chen, C. Recent Advances in Small Molecule Antagonists of the Corticotropin-Releasing Factor Type-1 Receptor-Focus on Pharmacology and Pharmacokinetics. Current Medicinal Chemistry, 2006, 13, 1261-1282.
Co-pending U.S. Appl. No. 18/241,804, inventors BArnes; Christopher et al., filed Sep. 1, 2023.
Million et al. A novel water-soluble selective CRF1 receptor antagonist, NBI 35965, blunts stress-induced visceral hyperalgesia and colonic motor function in rats. Brain Research, vol. 985, Issue 1, 2003, pp. 32-42.
Morabbi et al. Pexacerfont as a CRF1 antagonist for the treatment of withdrawal symptoms in men with heroin/methamphetamine dependence: a randomized, double-blind, placebo-controlled clinical trial. International Clinical Psychopharmacology 2017, vol. 00, No. 00. 9 pages.
Speiser et al. Congenital Adrenal Hyperplasia Due to Steroid 21-Hydroxylase Deficiency: An Endocrine Society Clinical Practice Guideline. J Clin Endocrinol Metab. 2010: 95(9): 4133-4160.
U.S. Appl. No. 16/639,540 Office Action dated Sep. 28, 2023.
U.S. Appl. No. 18/078,649 Office Action dated Sep. 8, 2023.
U.S. Appl. No. 18/307,718 Office Action dated Oct. 12, 2023.
Zorrilla et al. Progress in corticotropin-releasing factor-1 antagonist development. NIH Public Access—Author Manuscript provided (2011). 24 pages. Published in final edited form as: Drug Discov Today 2010; 15(9-10): 371-383.
Anonymous. A Study of Safety and Efficacy of Tildacerfont in Females With Polycystic Ovary Syndrome and Elevated Adrenal Androgens. Sep. 28, 2023 (Sep. 28, 2023). XP093131604. Retrieved from the Internet: URL: https://clinicaltrials.gov/study/NCT05370521 [retrieved on Feb. 14, 2024] (post-published).
Co-pending U.S. Appl. No. 18/438,060, inventors Ghosh; Sangita et al., filed Feb. 9, 2024.
EP21856734.5 Extended European Search Report dated Feb. 23, 2024.
Puttabyatappa, et al. Ovarian and Extra-Ovarian Mediators in the Development of Polycystic Ovary Syndrome. J Mol Endocrinol. Oct. 16, 2018;61(4): R161-R184. doi: 10.1530/JME-18-0079.
Sadeghi, et al. Polycystic Ovary Syndrome: A Comprehensive Review of Pathogenesis, Management, and Drug Repurposing. Int J Mol Sci. Jan. 6, 2022;23(2):583. doi: 10.3390/ijms23020583.
U.S. Pat. No. 10,849,908—*Neurocrine Biosciences, Inc.* (Petitioner) v. *Spruce Biosciences, Inc.* (Patent Owner). Decision Granting Institution of Post-Grant Review dated Dec. 1, 2023. 57 pages.
U.S. Appl. No. 13/063,226 Notice of Allowance dated Aug. 21, 2013.
U.S. Appl. No. 13/063,226 Office Action dated Jan. 24, 2013.
U.S. Appl. No. 18/307,718 Notice of Allowance dated Feb. 14, 2024.
Do, Hien-Quang et al.; Copper-catalyzed arylation of C-H bonds; Abstracts of Papers, 236th ACS National Meeting, New Orleans, LA, Apr. 6-10, 2008, Accession No. 2008:390596.
Mori. Polycystic Ovarian Syndrome-concept, Recent Treatment. Journal of Japan Endocrine Science 63(12):1449-1457 (1987).
*Neurocrine Biosciences, Inc.* (Petitioner) v. *Spruce Biosciences, Inc.* (Patent Owner). Decision Granting Institution of Post-Grant Review of U.S. Pat. No. 11,007,201 dated Dec. 1, 2023 (pp. 1-38) (PGR2022-00025).
*Neurocrine Biosciences, Inc.* (Petitioner) v. *Spruce Biosciences, Inc.* (Patent Owner). Petition for Post Grant Review of U.S. Pat. No. 10,849,908 dated May 28, 2021 (pp. 1-90) (PGR2021-00088).
*Neurocrine Biosciences, Inc.* (Petitioner) v. *Spruce Biosciences, Inc.* (Patent Owner). Petition for Post Grant Review of U.S. Pat. No. 11,007,201 dated Feb. 18, 2022 (pp. 1-92) (PGR2022-00025).
U.S. Appl. No. 16/639,540 Office Action dated Mar. 28, 2024.
U.S. Appl. No. 16/639,541 Office Action dated Apr. 4, 2022.
U.S. Appl. No. 17/586,228 Office Action dated Mar. 30, 2022.
U.S. Appl. No. 18/078,649 Office Action dated Mar. 21, 2024.

* cited by examiner

METHODS AND COMPOSITIONS FOR TREATING POLYCYSTIC OVARY SYNDROME

CROSS-REFERENCE

This application is a continuation of PCT Application No. PCT/US2021/045780, filed Aug. 12, 2021; which claims the benefit of U.S. Provisional Patent Application No. 63/064,863, filed Aug. 12, 2020; which are incorporated herein by reference in their entirety.

BACKGROUND

Polycystic ovary syndrome (PCOS) is one of the most common endocrine disorders affecting an estimated 12% of reproductive aged women. Women with PCOS may have polycystic ovarian morphologic features, ovulatory dysfunction in the form of infrequent or prolonged menstrual periods, and hyperandrogenism in the form of excess male hormone levels. This complex disorder has both environmental influences, such as obesity and insulin resistance, and inappropriate endocrine signaling from the hypothalamus and pituitary glands as contributors. Hyperandrogenism presents clinically as hirsutism and acne and biochemically with elevated serum androgen levels. Androgen and androgen precursors can be produced and secreted by the ovaries and also by the adrenal cortices in about the same amount in response to stimulation by pituitary derived luteinizing hormone (LH) to the ovaries and adrenocorticotropic hormone (ACTH) to the adrenal gland, respectively. Emerging data indicate that PCOS patients can be categorized according to whether the source of excessive androgen is primarily from the ovaries, namely, functional ovarian hyperandrogenism (FOH), or the adrenal glands, namely, functional adrenal hyperandrogenism (FAH), both (FOH and FAH), or neither and attributable to either insulin resistance/obesity or of unknown origin. A majority or about two-thirds of cases have functionally typical PCOS (PCOS-T) that is due to typical FOH, characterized by hyperresponsiveness of 17-hydroxyprogesterone (17-OHP). About one fifth of cases have functionally atypical FOH (PCOS-A), lacking 17-OHP hyperresponsiveness. Within these two FOH populations, about one-third may have both FOH and FAH. About 8% of PCOS cases are attributed to either obesity and the remainder are unknown or idiopathic in nature. Only about 3-5% PCOS cases are due to isolated FAH with androgen responsiveness to ACTH.

SUMMARY

Adrenal androgen excess in PCOS appears to occur independently of ovarian androgen excess, suggesting it may represent an intrinsic, and possible primary source of abnormal synthesis of adrenal androgens. Adrenal androgen excess of PCOS may not result from deficiencies in specific enzymatic steps, rather it may represent an altered pituitary responsivity to corticotropin releasing factor (CRF) and adrenocorticotropic hormone (ACTH).

In an aspect, the present disclosure provides methods for treating polycystic ovary syndrome with functional ovarian hyperandrogenism and functional adrenal hyperandrogenism (PCOS–FOH+FAH) in a subject in need thereof, comprising administering a CRF1 antagonist or pharmaceutically acceptable salt thereof.

In another aspect, the present disclosure provides methods for treating polycystic ovary syndrome with functional adrenal hyperandrogenism (PCOS-FAH) in a subject in need thereof, comprising administering a CRF1 antagonist or pharmaceutically acceptable salt thereof.

In another aspect, the present disclosure provides methods for treating polycystic ovary syndrome (PCOS) in a subject in need thereof, comprising administering a CRF1 antagonist or pharmaceutically acceptable salt thereof.

In another aspect, the present disclosure provides methods for treating polycystic ovary syndrome (PCOS) in a subject in need thereof, comprising accessing a source of excessive androgen; and administering a CRF1 antagonist or pharmaceutically acceptable salt thereof. In some embodiments, the cosyntropin is administered at a dose about 1 μg/m². In some embodiments, the cosyntropin is administered at a dose about 10 μg/m². In some embodiments, the cosyntropin is administered at a dose about 250 μg/m². In some embodiments, the source of excessive androgen is adrenal glands. In some embodiments, the source of excessive androgen is ovaries.

In some embodiments, the $CRF_1$ antagonist is a compound of Formula (I):

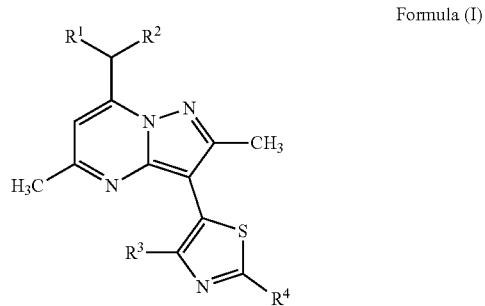

Formula (I)

or a pharmaceutically acceptable salt thereof, wherein: $R^1$ and $R^2$ are independently ethyl or n-propyl; $R^3$ is hydrogen, F, Cl, Br, methyl, trifluoromethyl, or methoxy; $R^4$ is hydrogen, Br, —$NR^aR^b$, methoxymethyl, n-butyl, acetamido, pyridin-4-yl, morpholin-4-yl,

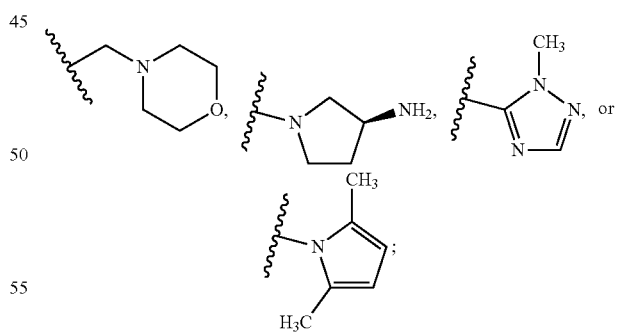

$R^a$ and $R^b$ are independently hydrogen, $C_1$-$C_3$alkyl, —$CH_2CH_2NH_2$, —$CH_2CH_2NHC(O)OC(CH_3)_3$, or —$CH_2CH_2NHCH_2CH_2CH_3$.

In some embodiments, $R^3$ is F, Cl, Br, methyl, or trifluoromethyl.

In some embodiments, $R^3$ is Cl or Br.

In some embodiments, $R^4$ is —$NR^aR^b$, pyridin-4-yl, morpholin-4-yl, or

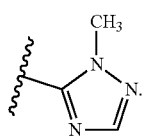

In some embodiments, R⁴ is morpholin-4-yl or

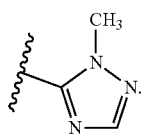

In some embodiments, R⁴ is —NR$^a$R$^b$, and R$^a$ and R$^b$ are independently $C_1$-$C_3$alkyl.

In some embodiments, the $CRF_1$ antagonist or a pharmaceutically acceptable salt thereof is 3-[4-bromo-2-(2-methyl-2H-[1,2,4]triazol-3-yl)-thiazol-5-yl]-2,5-dimethyl-7-(1-propyl-butyl)-pyrazolo[1,5-a]pyrimidine.

In some embodiments, the $CRF_1$ antagonist or a pharmaceutically acceptable salt thereof is 3-(4-bromo-2-(2-methyl-2H-[1,2,4]triazol-3-yl)-thiazol-5-yl)-7-(1-ethyl-propyl)-2,5-dimethyl-pyrazolo[1,5-a]pyrimidine.

In some embodiments, the $CRF_1$ antagonist or a pharmaceutically acceptable salt thereof is 3-(4-chloro-2-morpholin-4-yl-thiazol-5-yl)-7-(1-ethyl-propyl)-2,5-dimethyl-pyrazolo[1,5-a]pyrimidine.

In some embodiments, the $CRF_1$ antagonist is

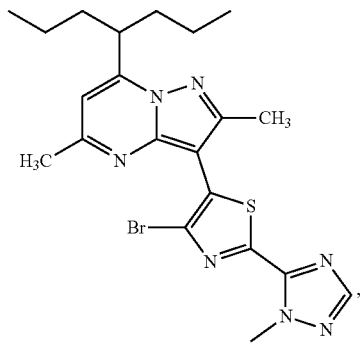 [SMILES: CCCC(CCC)c1cc(C)nc2c(-c3sc(-c4ncnn4C)nc3Br)c(C)nn12]

or a pharmaceutically acceptable salt thereof.

In some embodiments, the $CRF_1$ antagonist is

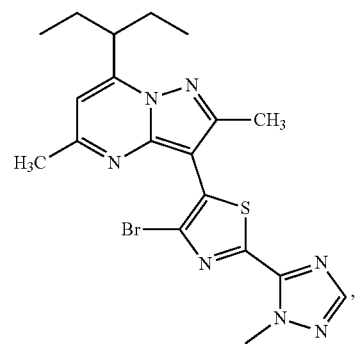 [SMILES: CCC(CC)c1cc(C)nc2c(-c3sc(-c4ncnn4C)nc3Br)c(C)nn12]

or a pharmaceutically acceptable salt thereof.

In some embodiments, the compound is

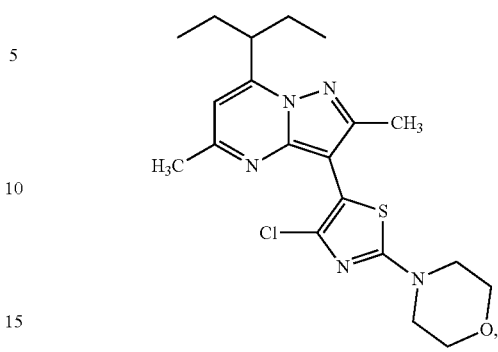

or a pharmaceutically acceptable salt thereof.

In some embodiments, the $CRF_1$ antagonist or pharmaceutically acceptable salt thereof is selected from the group consisting of: Antalarmin hydrochloride, CP-154,526, CP-376395 hydrochloride, NBI 27914 hydrochloride, NBI 35965 hydrochloride, NGD 98-2 hydrochloride, Pexacerfont, R 121919 hydrochloride, SSR125543 (crinecerfont), and SN003.

In some embodiments, the $CRF_1$ antagonist or pharmaceutically acceptable salt is administered in a dose of about 5 mg to about 400 mg total daily dose to the subject. In some embodiments, the $CRF_1$ antagonist or pharmaceutically acceptable salt is administered in a dose of about 300 mg total daily dose to the subject. In some embodiments, the $CRF_1$ antagonist or pharmaceutically acceptable salt is administered in a dose of about 200 mg total daily dose to the subject. In some embodiments, the $CRF_1$ antagonist or pharmaceutically acceptable salt is administered in a dose of about 150 mg total daily dose to the subject. In some embodiments, the $CRF_1$ antagonist or pharmaceutically acceptable salt is administered in a dose of about 100 mg total daily dose to the subject. In some embodiments, the $CRF_1$ antagonist or pharmaceutically acceptable salt is administered in a dose of about 75 mg total daily dose to the subject. In some embodiments, the $CRF_1$ antagonist or pharmaceutically acceptable salt is administered in a dose of about 50 mg total daily dose to the subject. In some embodiments, the $CRF_1$ antagonist or pharmaceutically acceptable salt is administered in a dose of about 25 mg total daily dose to the subject. In some embodiments, the $CRF_1$ antagonist or pharmaceutically acceptable salt is administered in a dose of about 10 mg total daily dose to the subject. In some embodiments, the $CRF_1$ antagonist or pharmaceutically acceptable salt thereof is administered as a pharmaceutical composition.

In some embodiments, an adrenocorticotropic hormone (ACTH) level is reduced by at least 5% from baseline. In some embodiments, an adrenocorticotropic hormone (ACTH) level is reduced by at least 10% from baseline. In some embodiments, a dehydroepiandrosterone sulfate (DHEAS) level is reduced by at least 5% from baseline. In some embodiments, a dehydroepiandrosterone sulfate (DHEAS) level is reduced by at least 10% from baseline. In some embodiments, the androstenedione (A4) level is reduced by at least 5% from baseline. In some embodiments, the androstenedione (A4) level is reduced by at least 10% from baseline. In some embodiments, the 1β-hydroxyandrostenedione (11OHA4) level is reduced by at least 5% from baseline. In some embodiments, the 1β-hydroxyandrostenedione (11OHA4) level is reduced by at least 10% from baseline. In some embodiments, the 11β-hydroxytestosterone (11OHT) level is reduced by at least 5% from baseline. In some embodiments, the 11β-hydroxytestosterone (11OHT) level is reduced by at least 10% from baseline.

In some embodiments, a reduced ACTH, DHEAS, A4, 11OHA4 or 11OHT level from baseline is maintained for at least 24 hours. In some embodiments, a reduced ACTH, DHEAS, A4, 11OHA4 or 11OHT level from baseline is maintained for at least 4 weeks.

In another aspect, the present disclosure provides methods for treating polycystic ovary syndrome with functional adrenal hyperandrogenism (PCOS-FAH) in a subject in need thereof, comprising administering a pharmaceutical composition comprising Compound 3:

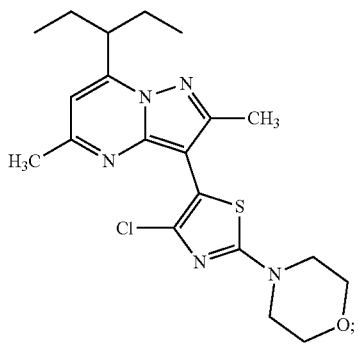 [SMILES: CCC(CC)c1cc(C)nc2c(-c3sc(N4CCOCC4)nc3Cl)c(C)nn12]

or a pharmaceutically acceptable salt or solvate thereof.

In another aspect, the present disclosure provides methods for treating polycystic ovary syndrome with functional ovarian hyperandrogenism and functional adrenal hyperandrogenism (PCOS–FOH+FAH) in a subject in need thereof, comprising administering a pharmaceutical composition comprising Compound 3:

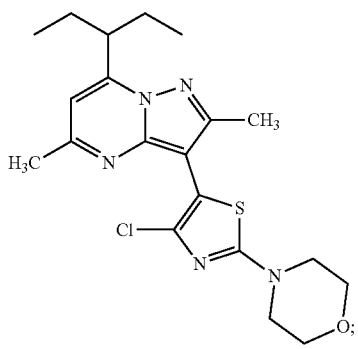 [SMILES: CCC(CC)c1cc(C)nc2c(-c3sc(N4CCOCC4)nc3Cl)c(C)nn12]

or a pharmaceutically acceptable salt or solvate thereof.

In some embodiments, the Compound 3 is administered at a dose between about 1 mg/day and about 400 mg/day.

In some embodiments, the pharmaceutical composition comprises about 25 mg of Compound 3, or a pharmaceutically acceptable salt or solvate thereof. In some embodiments, the pharmaceutical composition comprises about 50 mg of Compound 3, or a pharmaceutically acceptable salt or solvate thereof. In some embodiments, the pharmaceutical composition comprises between about 75 mg of Compound 3, or a pharmaceutically acceptable salt or solvate thereof. In some embodiments, the pharmaceutical composition comprises about 100 mg of Compound 3, or a pharmaceutically acceptable salt or solvate thereof. In some embodiments, the pharmaceutical composition comprises about 200 mg of Compound 3, or a pharmaceutically acceptable salt or solvate thereof. In some embodiments, the pharmaceutical composition comprises between about 1 mg and about 300 mg of Compound 3, or a pharmaceutically acceptable salt or solvate thereof.

In some embodiments, the pharmaceutical composition is in the form of microparticles. In some embodiments, the average size of the microparticles is between about 1 μm to about 20 μm. In some embodiments, the average size of the microparticles is between about 5 μm to about 15 μm. In some embodiments, the average size of the microparticles is less than about 10 μm.

In some embodiments, the pharmaceutical composition is in the form of a capsule or a tablet. In some embodiments, the capsule is a hard gelatin capsule. In some embodiments, the capsule is a soft gelatin capsule.

In some embodiments, the capsule is formed using materials selected from the group consisting of natural gelatin, synthetic gelatin, pectin, casein, collagen, protein, modified starch, polyvinylpyrrolidone, acrylic polymers, cellulose derivatives, and any combinations thereof. In some embodiments, the pharmaceutical composition is free of additional excipients. In some embodiments, the pharmaceutical composition further comprises one or more pharmaceutically acceptable excipients. In some embodiments, the pharmaceutical composition is in the form of a tablet. In some embodiments, the pharmaceutical composition further comprises one or more pharmaceutically acceptable excipients.

In some embodiments, the subject is a pediatric patient. In some embodiments, the subject is from about 9 years old to about 18 years old. In some embodiments, the subject is from about 8 years of age to about 55 years of age. In some embodiments, the subject is an adult patient.

In some embodiments, the subject is treated for a period of about 2 weeks to about 36 weeks. In some embodiments, the subject is treated for a period of about 1 month to 12 months. In some embodiments, the subject is treated for a period of about 10 months to 50 years.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Polycystic Ovary Syndrome (PCOS)

Polycystic ovarian syndrome (PCOS) is a heterogeneous disorder with multiple phenotypes and is one of the most common endocrine metabolic disorders in reproductive aged women. PCOS was first diagnosed and described as a syndrome of oligo-amenorrhea and polycystic ovaries that was variably accompanied by hirsutism, acne, and obesity.

Table 1 below. Androgen excess can be derived from the ovaries, the adrenal glands, both, or neither. Primary PCOS is the most common variety of PCOS without any known cause and a proposed theory suggests that functional ovarian hyperandrogenism (FOH) along with disturbance of hypothalamo-pituitary-ovarian (HPO) axis function may be the underlying cause. Further, functional adrenal hyperandrogenism (FAH) other than HPO axis disturbance may be explained for a certain population of PCOS patients.

The PCOS patients with primary FAH may experience an average 50% increase in adrenal volume that correlates with hyperandrogenemia severity.

TABLE 1

Functional classification of PCOS based on source of androgen excess

| PCOS Functional Type | Source of Androgen | GnRHag Test 17OHP Response | DAST Testosterone Response | ACTH test DHEA Response | Prevalence Among PCOS |
|---|---|---|---|---|---|
| PCOS-T | Primary FOH (typical FOH) | High$^a$ | High in 92.5% | High in 28% (associated FAH) | 67%$^b$ |
| PCOS-A | Primary FOH (atypical FOH) | Normal$^a$ | High | High in 30% (associated FAH) | 20% |
| | Primary FAH (isolated FAH) | Normal | Normal | High | 5% |
| | PCOS without FOH or FAH (PCOS-A of obesity or idiopathic PCOS-A) | Normal | Normal | Normal | 8% |

There are various diagnostic criteria for adolescent and adult patients considering the core diagnostic features, such as hyperandrogenism, persistent ovulatory dysfunction, and polycystic ovarian morphology (PCOM). The exact etiology of this disorder is not entirely clear, however, both genetic and environmental factors seem to play roles in causing the disorder. Generally, PCOS presents as a phenotype reflecting a self-perpetuating vicious cycle involving neuroendocrine, metabolic, and ovarian dysfunction and is characterized by excessive ovarian and/or adrenal androgen secretion. For example, intrinsic ovarian factors such as altered steroidogenesis and factors external to the ovary such as hyperinsulinemia contribute to the excessive ovarian androgen production. The classic ovarian phenotype of enlarged ovaries with string-of-pearl morphology and theca interstitial hyperplasia reflects androgen exposure; this morphology has also been observed in women with congenital adrenal hyperplasia (CAH).

In order to attempt to understand the pathophysiology of PCOS, it is important to understand the molecular basis of steroidogenesis and androgen source, production and physiology. Under normal circumstances in women, the ovaries and adrenal glands contribute about equally to testosterone production. Approximately half of testosterone originates from direct testosterone secretion by the ovaries and adrenal glands, whereas half is produced by peripheral conversion of circulating androstenedione, which itself arises from approximately equal ovarian and adrenal secretion. Androgen production is not under direct negative feedback regulation by the neuroendocrine system in females, as is the case for estradiol and cortisol secretion. Androgens are secreted by both the ovaries and adrenal glands in response to their respective tropic hormones, LH and ACTH. The zona reticularis of the adrenal gland resembles the theca cell compartment of the ovary in its expression of the core enzymatic pattern for androgen production.

PCOS patients can be functionally categorized as distinct subtypes based on the source of androgen excess listed in Test procedures to determine the source of androgen are listed below in Table 2. The ovarian hyperandrogenism of PCOS is demonstrated directly by the GnRHag test or the hCG test and in combination with the dexamethasone androgen-suppression test (DAST). The GnRHag test determines the coordinated function of the ovarian follicle. Leuprolide acetate 10 µg/kg sc (or a comparable dose of any other short-acting GnRHag) stimulates endogenous LH and FSH release that peaks at 3-4 hours and persists for 24 hours; this in turn stimulates increased secretion of sex steroids and their precursors, with serum levels peaking at 18-24 hours. In the absence of evidence of a steroidogenic block, an elevated 17OHP response is typical of PCOS. Ovarian steroidogenic enzyme deficiency, which is rare, can be detected by an abnormal pattern of steroid intermediates in response to the test. hCG is an LH analog: 5000 IU intramuscularly stimulates steroidogenic responses comparable with those of a GnRHag test at 24 hours. DAST indirectly tests for ovarian source of androgens by suppressing ACTH-dependent androgen production of androgens. In the presence of normal adrenocortical suppression an inappropriately elevated serum testosterone post-DAST indicates an ACTH-independent source of androgen, which is ordinarily of ovarian origin.

Adrenal hyperandrogenism may be demonstrated by a rapid ACTH test: cosyntropin is administered iv and peak steroid responses occur at 15-60 minutes. An elevated DHEA post this test indicates an ACTH-dependent source of androgen, which is ordinarily of adrenal origin. The test may be performed using cosyntropin 250 µg, this is a supramaximal dose. Lower doses of cosyntropin may be used (10 µg/m2) which elicit a similar peak response. A low-dose ACTH test (1.0-µg cosyntropin) may be used and may be more physiologic. It usually elicits nearly as great a peak response that promptly wanes, and in PCOS, does not elicit such a wide spectrum of elevated steroid intermediates as do larger doses.

TABLE 2

Methods to determine source of female androgen excess

| Test | Rationale | Method | Outcome Measures | Interpretation[a] |
|---|---|---|---|---|
| GnRHag | Endogenous LH and FSH release stimulates coordinated funcion of ovarian follicles | Leuprolide acetate 10 µg/kg sc (for maximum stimulation) | Ovarian steroid secretion peaks at 20-24 h | 17OHP >152 ng/dL without steroidogenic blocs indicates typical FOH (PCOS-T) |
| hCG | Exogenous administration of LH analog stimulates theca-intersstitial cells | hCG 3000 IU/m$^2$ (for maximum stimulation) | Ovarian steroid secretion peaks at 24 h | 17OHP >152 ng/dL without steroidogenic block indicates typical FOH (PCOS-T) |
| LDAST | Long DAST: dexamethasone profoundly suppreses adrenal androgens over several days | Dexamethasone 0.5 mg QID per os × 4-5 d | Free testosterone, DHEAS, cortisol: sample early morning d 5 | Free testosterone ≥8 pg/mL with DHEAS <70 and cortisol <1 µg/dL characteristic of FOH |
| SDAST | Short DAST: dexamethasone rapidly suppresses adrenal testosterone and cortisol | Dexamethasone 0.25 mg/m$^2$ per os at 12 noon | Total testosterone, cortisol: sample 4 PM (4 h) | Total testosterone >26 ng/mL, cortisol <5 µg/dl suggests FOH |
| ACTH | Exogenous ACTH stimulates adrenal steroidogenesis | Cosyntropin ≥10 µg/m$^2$ (for maximum stimulation) | DHEA, 17OHP, steroid intermediates, cortisol peak at 30-60 min | DHEA 1500-3000 µg/dL without steroidogenic block indicates FAH |

Corticotropin Releasing Factor

Currently, no single universal treatment for PCOS is available. As a result, current treatments tend to be individualized and adapted to the actual needs of the individual patient. Furthermore, treatment may be symptom-oriented. For example, targets for pharmacological treatment may include androgen excess. For PCOS patients with elevated adrenal androgens, FOH+FAH and PCOS-FAH patients, in some embodiments, pharmacological treatment, such as corticotropin releasing factor (CRF) receptor antagonist targeting ACTH production may be used.

Corticotropin releasing factor (CRF) is a 41 amino acid peptide that is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in the brain. There is also evidence that CRF plays a significant role in integrating the response in the immune system to physiological, psychological, and immunological stressors.

CRF has been implicated in psychiatric disorders and neurological diseases including depression and anxiety, as well as the following: Alzheimer's disease, Huntington's disease, progressive supranuclear palsy, amyotrophic lateral sclerosis, Parkinson's disease, epilepsy, migraine, alcohol and substance abuse and associated withdrawal symptoms, obesity, metabolic syndrome, congenital adrenal hyperplasia (CAH), Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary derived tumors, chronic fatigue syndrome, and fibromyalgia.

CRF is believed to be the major physiological regulator of the basal and stress-induced release of adrenocorticotropic hormone ("ACTH"), O-endorphin, and other proopiomelanocortin ("POMC")-derived peptides from the anterior pituitary. Secretion of CRF causes release of ACTH from corticotrophs in the anterior pituitary via binding to the $CRF_1$ receptor, a member of the class B family of G-protein coupled receptors.

Due to the physiological significance of $CRF_1$, the development of biologically-active small molecules having significant CRF receptor binding activity and which are capable of antagonizing the $CRF_1$ receptor remains a desirable goal and has been the subject of ongoing research and development for the treatment of anxiety, depression, irritable bowel syndrome, post-traumatic stress disorder, and substance abuse, and congenital adrenal hyperplasia.

The pituitary hormone ACTH, under the control of hypothalamic corticotropin-releasing factor (CRF), stimulates uptake of cholesterol and drives the synthesis of pregnenolone initiating steroidogenesis in the adrenal gland. The adrenal cortex is comprised of three zones, which produce distinct classes of hormones many of which are driven by ACTH mobilizing cholesterol through this pathway. The middle layer, the zona reticularis is responsible for the production of androgens such as DHEA, DHEAS and androstenedione, (A4) the precursor to testosterone (T) and dihydrotestosterone (DHT). This layer is also responsible for the production of the 11-oxyandrogens, 11β-hydroxyandrostenedione (11OHA4) and 11β-hydroxytestosterone (11OHT), which are major bioactive androgens, particularly in women. Due to an unknown cause in PCOS patients with elevated androgens, the zone reticularis displays a hyperresponsiveness to ACTH resulting excessive levels of DHEA, DHEAS, 11OHA4, 11OHT and A4. The excessive ACTH stimulation causes hypertrophy of the zona reticularis resulting in adrenal hyperplasia and clinically manifests with physical features typical of PCOS and hyperandrogenism. Reducing the stimulatory effect on the pituitary's ACTH secretion by inhibiting the $CRF_1$ receptor is expected is reduce excessive androgen synthesis from the ACTH responsive zone of the adrenal gland in PCOS. The normalization of elevated androgen levels in the short term would be expected to ameliorate cardinal features of PCOS—hirsutism, acne and menstrual irregularities—over the long term.

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a," "an," and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes 10% level of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

"Alkyl" refers to a straight or branched hydrocarbon chain radical consisting solely of carbon and hydrogen atoms, containing no unsaturation, and preferably having from one to five carbon atoms (i.e. $C_1$-$C_5$alkyl). In some embodiments, an alkyl comprises one to four carbon atoms (i.e., $C_1$-$C_4$alkyl).). In some embodiments, an alkyl comprises one to three carbon atoms (i.e., $C_1$-$C_3$alkyl).). In some embodiments, an alkyl comprises one to two carbon atoms (i.e., $C_1$-$C_2$alkyl). In some embodiments, an alkyl comprises one carbon atom (i.e., Cialkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (isobutyl), 1,1-dimethylethyl (tert-butyl), or 1-pentyl (n-pentyl). The alkyl is attached to the rest of the molecule by a single bond. Unless stated otherwise specifically in the specification, an alkyl group is optionally substituted by one or more substituents such as those described herein.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. "Administering" a pharmaceutical composition may be accomplished by injection, topical administration, and oral administration or by other methods alone or in combination with other known techniques.

By "pharmaceutically acceptable", it is meant the carrier, diluent or excipient must be compatible with the other ingredients of the composition and not deleterious to the recipient thereof.

The term "pharmaceutical composition" means a composition comprising at least one active ingredient, such as a steroid or a pharmaceutically acceptable salt thereof or a $CRF_1$ antagonist or a pharmaceutically acceptable salt thereof, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "supraphysiologic amount" describes glucocorticoid dose levels that are above the daily glucocorticoid requirement (production rate) found in healthy individuals.

The term "physiologic amount" describes glucocorticoid dose levels that meet the daily glucocorticoid requirement (production rate) found in healthy individuals.

The term "hydrocortisone equivalents" as used herein is understood by a person skilled in the art to be the conversion calculations needed to be considered when substituting one glucocorticoid for another as the potency and duration of action of various glucocorticoids may vary. Hence, the term "hydrocortisone equivalents" is the standard used for comparison of glucocorticoid potency.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

Compounds

Disclosed herein are $CRF_1$ antagonists or pharmaceutically acceptable salt thereof such as Antalarmin hydrochloride, CP-154,526, CP-376395 hydrochloride, NBI 27914 hydrochloride, NBI 35965 hydrochloride, NGD 98-2 hydrochloride, Pexacerfont, R 121919 hydrochloride, SN003, and SSR125543 (crinecerfont).

In one aspect, the $CRF_1$ antagonist or pharmaceutically acceptable salt thereof is selected from the group consisting of n-butyl-N-ethyl-2,5,6-trimethyl-7-(2,4,6-trimethylphenyl)-7H-pyrrolo[2,3-d]pyrimidin-4-amine hydrochloride (Antalarmin hydrochloride), n-butyl-N-ethyl-2,5-dimethyl-7-(2,4,6-trimethylphenyl)-7H-pyrrolo[2,3-d]pyrimidin-4-amine hydrochloride (Pfizer CP154526), N-(1-Ethylpropyl)-3,6-dimethyl-2-(2,4,6-trimethylphenoxy)-4-pyridinamine hydrochloride (Pfizer CP376395 hydrochloride), 5-Chloro-N-(cyclopropylmethyl)-2-methyl-n-propyl-N'-(2,4,6-trichlorophenyl)-4,6-pyrimidinediamine hydrochloride (NB127914 hydrochloride), (7S)-6-(Cyclopropylmethyl)-2-(2,4-dichlorophenyl)-7-ethyl-7,8-dihydro-4-methyl-6H-1,3,6,8a-tetraazaacenaphthylene hydrochloride (NB135965 hydrochloride), N-(1-Ethylpropyl)-3-methoxy-5-[2-methoxy-4-(trifluoromethoxy)phenyl]-6-methyl-2-pyrazinamine hydrochloride (NGD 98-2 hydrochloride), 8-(6-Methoxy-2-methyl-3-pyridinyl)-2,7-dimethyl-N-[(1R)-1-methylpropyl]pyrazolo[1,5-a]-1,3,5-triazin-4-amine (Pexacerfont), 3-[6-(Dimethylamino)-4-methyl-3-pyridinyl]-2,5-dimethyl-N,N-dipropylpyrazolo[1,5-a]pyrimidin-7-amine hydrochloride (R 121919 hydrochloride), and N-(4-Methoxy-2-methylphenyl)-1-[1-(methoxymethyl)propyl]-6-methyl-1H-1,2,3-triazolo[4,5-c]pyridine-4-amine (SN003), (S)-4-(2-chloro-4-methoxy-5-methylphenyl)-N-(2-cyclopropyl-1-(3-fluoro-4-methylphenyl)ethyl)-5-methyl-N-(prop-2-yn-1-yl)thiazol-2-amine (SSR125543).

Disclosed herein is a compound of Formula (I):

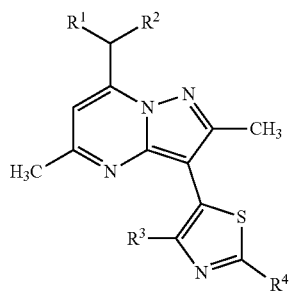

Formula (I)

or a pharmaceutically acceptable salt thereof, wherein $R^1$ and $R^2$ are independently ethyl or n-propyl; $R^3$ is H, Cl, Br, methyl, trifluoromethyl, or methoxy; $R^4$ is H, Br, —$NR^aR^b$, methoxymethyl, n-butyl, acetamido, pyridin-4-yl, morpholin-4-yl,

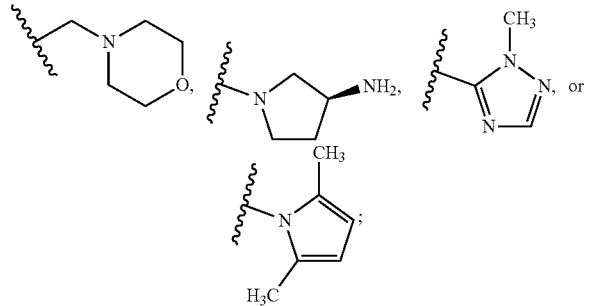

and
$R^a$ and $R^b$ are independently hydrogen, $C_1$-$C_3$alkyl, —$CH_2CH_2NH_2$, —$CH_2CH_2NHC(O)OC(CH_3)_3$, or —$CH_2CH_2NHCH_2CH_2CH_3$.

In some embodiments, $R^1$ and $R^2$ are independently ethyl or n-propyl. In some embodiments, $R^1$ is ethyl and $R^2$ is n-propyl. In some embodiments, $R^1$ is n-propyl and $R^2$ is ethyl. In some embodiments, $R^1$ and $R^2$ are both ethyl. In some embodiments, $R^1$ and $R^2$ are both n-propyl.

In some embodiments, $R^3$ is hydrogen, Cl, Br, methyl, or trifluoromethyl. In some embodiments, $R^3$ is hydrogen, Cl, Br, or methyl. In some embodiments, $R^3$ is hydrogen, Cl, or Br. In some embodiments, $R^3$ is hydrogen. In some embodiments, $R^3$ is Cl. In some embodiments, $R^3$ is Br.

In some embodiments, $R^4$ is hydrogen, Br, —$NR^aR^b$, methoxymethyl, n-butyl, acetamido, pyridin-4-yl, morpholin-4-yl,

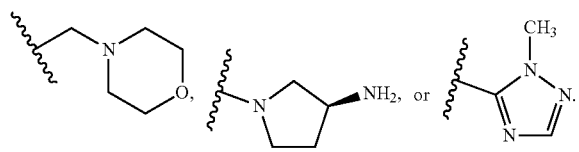

In some embodiments, $R^4$ is Br, —$NR^aR^b$, methoxymethyl, n-butyl, acetamido, pyridin-4-yl, morpholin-4-yl,

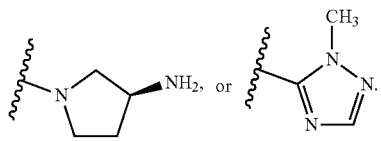

In some embodiments, $R^4$ is —$NR^aR^b$, methoxymethyl, n-butyl, acetamido, pyridin-4-yl, morpholin-4-yl, or

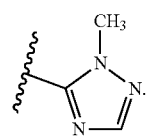

In some embodiments, $R^4$ is —$NR^aR^b$, n-butyl, acetamido, pyridin-4-yl, morpholin-4-yl, or

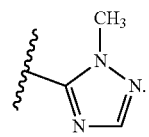

In some embodiments, $R^4$ is —$NR^aR^b$, pyridin-4-yl, morpholin-4-yl, or

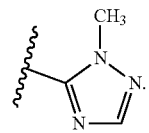

In some embodiments, $R^4$ is morpholin-4-yl or

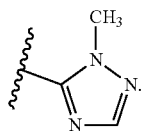

In some embodiments, $R^4$ is morpholin-4-yl. In some embodiments, $R^4$ is

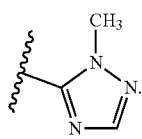

In some embodiments, $R^4$ is —$NR^aR^b$ and $R^a$ and $R^b$ are independently $C_1$-$C_3$alkyl.

Disclosed herein is a compound of Formula (II):

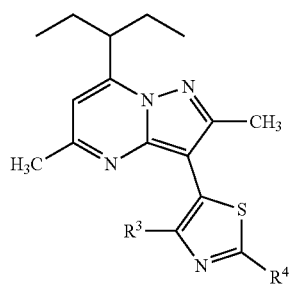

Formula (II)

or a pharmaceutically acceptable salt thereof, wherein $R^3$ is H, Cl, Br, methyl, trifluoromethyl, or methoxy; $R^4$ is H, Br, —$NR^aR^b$, methoxymethyl, n-butyl, acetamido, pyridin-4-yl, morpholin-4-yl,

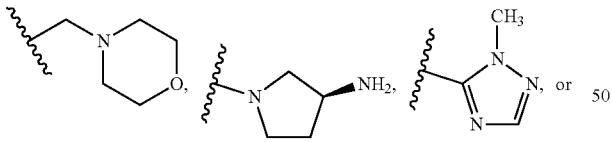

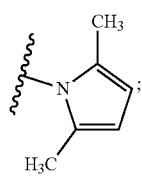

and $R^a$ and $R^b$ are independently hydrogen, $C_1$-$C_3$alkyl, —$CH_2CH_2NH_2$, —$CH_2CH_2NHC(O)OC(CH_3)_3$, or —$CH_2CH_2NHCH_2CH_2CH_3$—$CH_2CH_2NHCH_2CH_2CH_3$.

Disclosed herein is a compound of Formula (III):

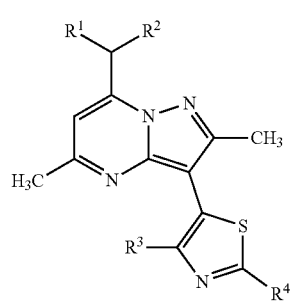

Formula (III)

or a pharmaceutically acceptable salt thereof, wherein $R^1$ and $R^2$ are n-propyl; $R^3$ is H, Cl, Br, methyl, trifluoromethyl, or methoxy; $R^4$ is H, Br, —$NR^aR^b$, methoxymethyl, n-butyl, acetamido, pyridin-4-yl, morpholin-4-yl,

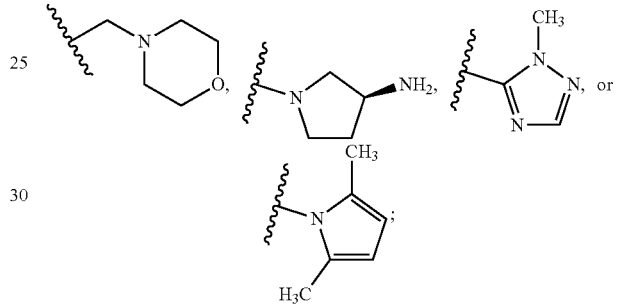

and $R^a$ and $R^b$ are independently hydrogen, $C_1$-$C_3$alkyl, —$CH_2CH_2NH_2$, —$CH_2CH_2NHC(O)OC(CH_3)_3$, or —$CH_2CH_2NHCH_2CH_2CH_3$.

Disclosed herein is a compound of Formula (IV):

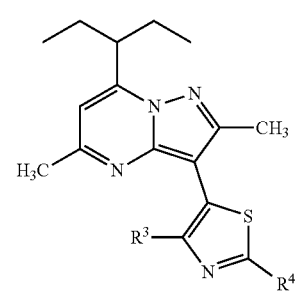

Formula IV or a pharmaceutically acceptable salt thereof, wherein $R^3$ is Cl, Br, methyl, trifluoromethyl, or methoxy; $R^4$ is H, Br, —$NR^aR^b$, methoxymethyl, n-butyl, acetamido, pyridin-4-yl, morpholin-4-yl,

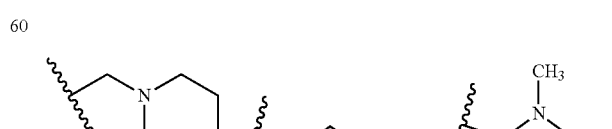

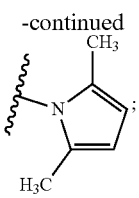

and $R^a$ and $R^b$ are independently hydrogen, $C_1$-$C_3$alkyl, —$CH_2CH_2NH_2$, —$CH_2CH_2NHC(O)OC(CH_3)_3$, or —$CH_2CH_2NHCH_2CH_2CH_3$.

For a compound or pharmaceutically acceptable salt of Formula (I), (II), (III), and (IV), $R^3$ may be hydrogen, Cl, Br, methyl, trifluoromethyl, or methoxy. For a compound or pharmaceutically acceptable salt of Formula (I), (II), (III), and (IV), $R^3$ may be Cl, Br, methyl, trifluoromethyl, or methoxy. For a compound or pharmaceutically acceptable salt of Formula (I), (II), (III), and (IV), $R^3$ may be Cl, Br, methyl, or trifluoromethyl. For a compound or pharmaceutically acceptable salt of Formula (I), (II), (III), and (IV), $R^3$ may be Cl, Br, or methyl. For a compound or pharmaceutically acceptable salt of Formula (I), (II), (III), and (IV), $R^3$ may be Cl. For a compound or pharmaceutically acceptable salt of Formula (I), (II), (III), and (IV), $R^3$ may be Br. For a compound or pharmaceutically acceptable salt of Formula (I), (II), (III), and (IV), $R^3$ may be methyl.

For a compound or pharmaceutically acceptable salt of Formula (I), (II), (III), and (IV), $R^4$ is Br, —$NR^aR^b$, methoxymethyl, n-butyl, acetamido, pyridin-4-yl, morpholin-4-yl,

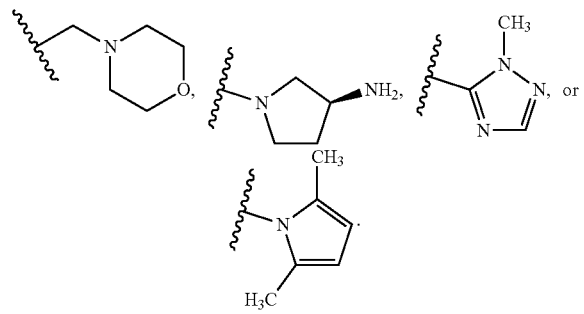

For a compound or pharmaceutically acceptable salt of Formula (I), (II), (III), and (IV), $R^4$ is Br, methoxymethyl, n-butyl, acetamido, pyridin-4-yl, morpholin-4-yl,

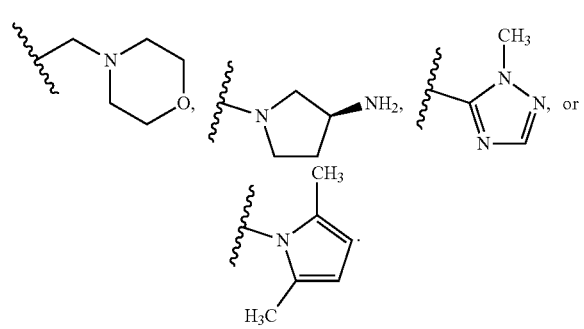

For a compound or pharmaceutically acceptable salt of Formula (I), (II), (III), and (IV), $R^4$ is Br, n-butyl, acetamido, pyridin-4-yl,

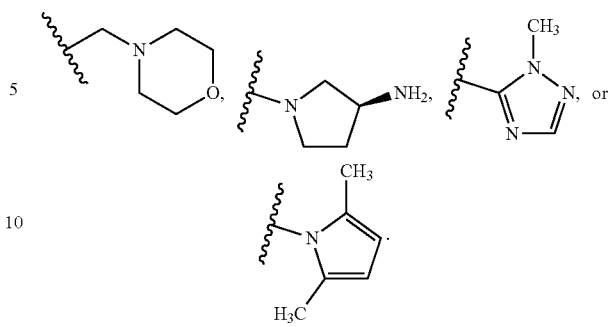

For a compound or pharmaceutically acceptable salt of Formula (I), (II), (III), and (IV), $R^4$ is Br, acetamido, pyridin-4-yl,

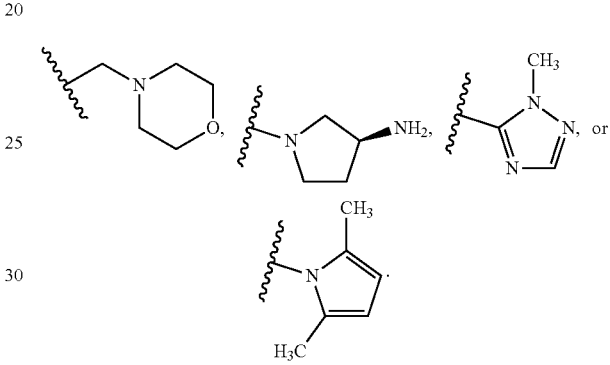

For a compound or pharmaceutically acceptable salt of Formula (I), (II), (III), and (IV), $R^4$ is Br, pyridin-4-yl,

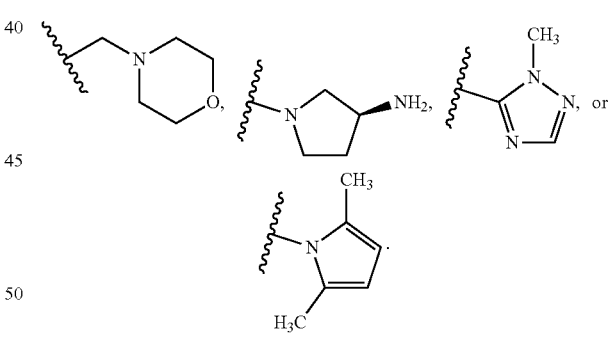

For a compound or pharmaceutically acceptable salt of Formula (I), (II), (III), and (IV), $R^4$ is pyridin-4-yl, morpholin-4-yl,

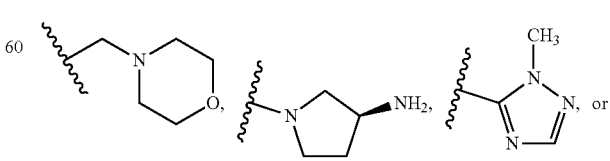

-continued

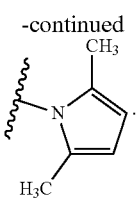

For a compound or pharmaceutically acceptable salt of Formula (I), (II), (III), and (IV), R⁴ is morpholin-4-yl,

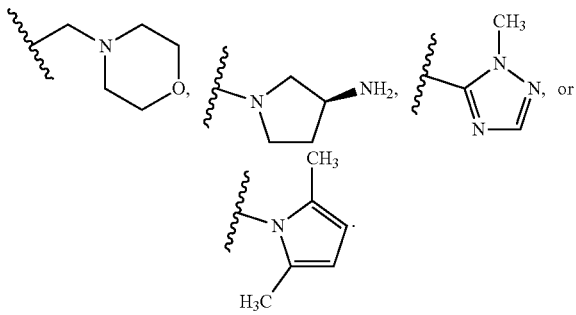

For a compound or pharmaceutically acceptable salt of Formula (I), (II), (III), and (IV), R⁴ is

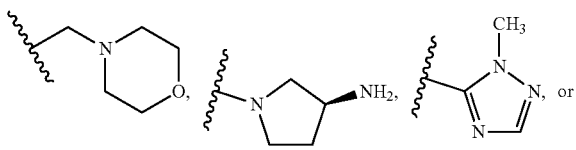

For a compound or pharmaceutically acceptable salt of Formula (I), (II), (III), and (IV), R⁴ is

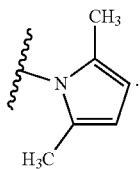

For a compound or pharmaceutically acceptable salt of Formula (I), (II), (III), and (IV), R⁴ is

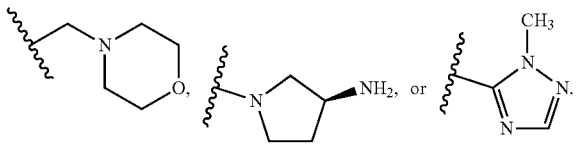

For a compound or pharmaceutically acceptable salt of Formula (I), (II), (III), and (IV), R⁴ is

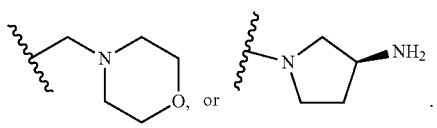 [SMILES: *CN1CCOCC1 ; "or" ; *N1CC[C@H](N)C1 ; "."]

For a compound or pharmaceutically acceptable salt of Formula (I), (II), (III), and (IV), R⁴ is

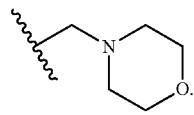 [SMILES: *CN1CCOCC1]

For a compound or pharmaceutically acceptable salt of Formula (I), (II), (III), and (IV), R⁴ is morpholin-4-yl.

Disclosed herein is 3-[4-bromo-2-(2-methyl-2H-[1,2,4] triazol-3-yl)-thiazol-5-yl]-2,5-dimethyl-7-(1-propyl-butyl)-pyrazolo[1,5-a]pyrimidine (Compound 1) or a pharmaceutically acceptable salt thereof:

Compound 1

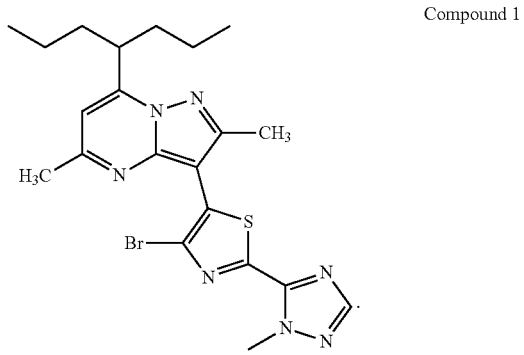 [SMILES: CCCC(CCC)c1cc(C)nc2c(-c3sc(-c4ncnn4C)nc3Br)c(C)nn12 ; "."]

Disclosed herein is 3-(4-bromo-2-(2-methyl-2H-[1,2,4] triazol-3-yl)-thiazol-5-yl)-7-(1-ethyl-propyl)-2,5-dimethyl-pyrazolo[1,5-a]pyrimidine (Compound 2) or a pharmaceutically acceptable salt thereof:

Compound 2

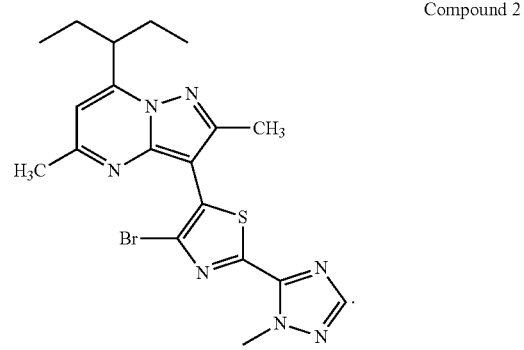 [SMILES: CCC(CC)c1cc(C)nc2c(-c3sc(-c4ncnn4C)nc3Br)c(C)nn12 ; "."]

Disclosed herein is 3-(4-Chloro-2-(morpholin-4-yl)thiazol-5-yl)-7-(1-ethylpropyl)-2,5-dimethylpyrazolo(1,5-a) pyrimidine (or alternatively 4-(4-chloro-5-(2,5-dimethyl-7-(pentan-3-yl)pyrazolo[1,5-a]pyrimidin-3-yl)thiazol-2-yl) morpholine) (Compound 3) or a pharmaceutically acceptable salt thereof:

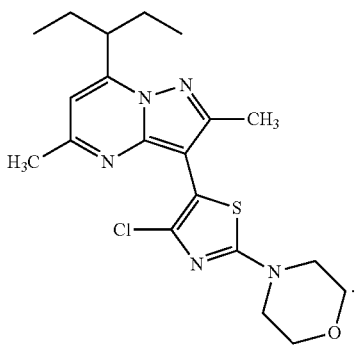

Compound 3

In some embodiments, 4-(4-chloro-5-(2,5-dimethyl-7-(pentan-3-yl)pyrazolo[1,5-a]pyrimidin-3-yl)thiazol-2-yl)morpholine is referred to as Compound 3. In some embodiments, 3-(4-Chloro-2-(morpholin-4-yl)thiazol-5-yl)-7-(1-ethylpropyl)-2,5-dimethylpyrazolo(1,5-a)pyrimidine is referred to as Compound 3.

In one aspect, the $CRF_1$ antagonist or pharmaceutically acceptable salt thereof may be an astressin. An astressin generally refers to a nonselective corticotropin releasing hormone antagonist that reduces the synthesis of ACTH and cortisol.

Pharmaceutical Compositions

Disclosed herein are pharmaceutical compositions comprising a compound or pharmaceutically acceptable salt described herein. In certain embodiments, the composition comprises a steroid or a pharmaceutically acceptable salt thereof and a $CRF_1$ antagonist or pharmaceutically acceptable salt thereof as disclosed above. In some embodiments, the steroid or a pharmaceutically acceptable salt thereof is exogenous glucocorticoids (GC) or a pharmaceutically acceptable salt thereof.

Dosage Form

In some embodiments, the pharmaceutical compositions described herein are provided in unit dosage form. As used herein, a "unit dosage form" is a composition containing an amount of a compound or pharmaceutically acceptable salt described herein that is suitable for administration to an animal, preferably mammal, subject in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

In some embodiments, the pharmaceutical compositions described herein are formulated as oral dosage forms. Suitable oral dosage forms include, for example, tablets, pills, sachets, or capsules. In some embodiments, the pharmaceutical composition comprises one or more additional pharmaceutically acceptable excipients. See, e.g., Remington: The Science and Practice of Pharmacy (Gennaro, 21st Ed. Mack Pub. Co., Easton, PA (2005) for a list of pharmaceutically acceptable excipients.

Capsule

In some embodiments, the pharmaceutical composition is formulated as a capsule. In some embodiments, the pharmaceutical composition is formulated as a hard gel capsule. In some embodiments, the pharmaceutical composition is formulated as a soft gel capsule.

In some embodiments, the capsule is formed using materials which include, but are not limited to, natural or synthetic gelatin, pectin, casein, collagen, protein, modified starch, polyvinylpyrrolidone, acrylic polymers, cellulose derivatives, or any combinations thereof. In some embodiments, the capsule is formed using preservatives, coloring and opacifying agents, flavorings and sweeteners, sugars, gastroresistant substances, or any combinations thereof. In some embodiments, the capsule is coated. In some embodiments, the coating covering the capsule includes, but is not limited to, immediate release coatings, protective coatings, enteric or delayed release coatings, sustained release coatings, barrier coatings, seal coatings, or combinations thereof. In some embodiments, a capsule herein is hard or soft. In some embodiments, the capsule is seamless. In some embodiments, the capsule is broken such that the particulates are sprinkled on soft foods and swallowed without chewing. In some embodiments, the shape and size of the capsule also vary. Examples of capsule shapes include, but are not limited to, round, oval, tubular, oblong, twist off, or a non-standard shape. The size of the capsule may vary according to the volume of the particulates. In some embodiments, the size of the capsule is adjusted based on the volume of the particulates and powders. Hard or soft gelatin capsules may be manufactured in accordance with conventional methods as a single body unit comprising the standard capsule shape. A single-body soft gelatin capsule typically may be provided, for example, in sizes from 3 to 22 minims (1 minims being equal to 0.0616 ml) and in shapes of oval, oblong or others. The gelatin capsule may also be manufactured in accordance with conventional methods, for example, as a two-piece hard gelatin capsule, sealed or unsealed, typically in standard shape and various standard sizes, conventionally designated as (000), (00), (0), (1), (2), (3), (4), and (5). The largest number corresponds to the smallest size. In some embodiments, the pharmaceutical composition described herein (e.g., capsule) is swallowed as a whole.

In some embodiments, the capsule comprises one or more pharmaceutically acceptable excipients. In some embodiments, the capsule is free of additional excipients.

In some embodiments, a capsule is developed, manufactured and commercialized for a drug substance that is insoluble. In some embodiments, a drug substance is insoluble if solubility is less than 0.002 mg/mL in water. In some embodiments, the capsule has a dose strength of up to 200 mg. In some embodiments, drug substance in the capsule is immediately released in a dissolution medium using USP apparatus I. In some embodiments, drug substance in the capsule is immediately released in a dissolution medium using USP apparatus II.

Tablet

Poorly soluble drugs may be difficult to formulate using standard technologies such as high shear wet granulation. Optimum delivery of poorly soluble drugs may require complex technologies such as solid solutions amorphous dispersions (hot melt extrusion or spray drying), nano-formulations or lipid-based formulations. Hydrophobic drug substances may be considered poorly soluble according to USP criteria and may be known to be difficult to granulate with water and other excipients. This is likely due to most known excipients for immediate release formulations being water soluble or water-swellable. Making a tablet of a high dose drug substance that is poorly soluble may require a high concentration of the drug substance. However, as the drug concentration is increased above a certain level, formation of granules may become more and more difficult. Furthermore, at a certain drug load, it may become impossible.

In some embodiments, the pharmaceutical composition is formulated as a tablet.

In some embodiments, the tablet is made by compression, molding, or extrusion, optionally with one or more pharmaceutically acceptable excipient. In some embodiments, compressed tablets are prepared by compressing a compound or pharmaceutically acceptable salt described herein in a free-flowing form, optionally mixed with pharmaceutically acceptable excipients. In some embodiments, molded tablets are made by molding a mixture of the powdered a compound or pharmaceutically acceptable salt described herein, moistened with an inert liquid diluent. In some embodiments, the tablet is prepared by hot-melt extrusion. In some embodiments, extruded tablets are made by forcing a mixture comprising a compound or pharmaceutically acceptable salt described herein, through an orifice or die under controlled conditions. In some embodiments, the tablet is coated or scored. In some embodiments, the tablet is formulated so as to provide slow or controlled release of a compound or pharmaceutically acceptable salt described herein. In some embodiments, a tablet is developed, manufactured and commercialized for a drug substance that is insoluble. In some embodiments, a drug substance is insoluble if solubility is less than 0.002 mg/mL in water. In some embodiments, the tablet has a dose strength of up to 200 mg. In some embodiments, drug substance in the tablet is immediately released in a dissolution medium using USP apparatus I. In some embodiments, drug substance in the tablet is immediately released in a dissolution medium using USP apparatus II.

In some embodiments, the tablet size is less than about 1000 mg, less than about 800 mg, less than about 600 mg, less than about 400 mg, less than about 200 mg, less than about 100 mg or less than 50 mg. In some embodiments, the tablet has a dose strength of more than about 10 mg, more than about 50 mg, more than about 100 mg, more than about 150 mg, more than about 200 mg, or more than about 250 mg. In some embodiments, the tablet size is less than about 1000 mg for a dose strength of more than about 50 mg. In some embodiments, the tablet size is less than 800 mg for a dose strength of more than about 100 mg. In some embodiments, the tablet size is less than 600 mg for a dose strength of more than about 150 mg. In some embodiment, the tablet size is less than 400 mg for a dose strength of more than about 200 mg. In some embodiments, the tablet size is less than 400 mg for a dose strength of 100 mg. In some embodiments, the tablet size is less than 200 mg for a dose strength of 50 mg. In some embodiments, the tablet size is less than 50 mg for a dose strength of 10 mg.

In some embodiments, more than about 20% of the tablet is dissolved in conventional dissolution media. In some embodiments, more than about 40% of the tablet is dissolved in conventional dissolution media. In some embodiments, more than about 50% of the tablet is dissolved in conventional dissolution media. In some embodiments, more than about 60% of the tablet is dissolved in conventional dissolution media. In some embodiments, more than about 70% of the tablet is dissolved in conventional dissolution media. In some embodiments, more than about 80% of the tablet is dissolved in conventional dissolution media. In some embodiments, more than about 20% of the tablet is dissolved in less than 24 hours in conventional dissolution media. In some embodiments, more than about 20% of the tablet is dissolved in less than 12 hours in conventional dissolution media. In some embodiments, more than about 20% of the tablet is dissolved in less than 6 hours in conventional dissolution media. In some embodiments, more than about 20% of the tablet is dissolved in less than 3 hours in conventional dissolution media. In some embodiments, more than about 20% of the tablet is dissolved in less than 2 hours in conventional dissolution media. In some embodiments, more than about 20% of the tablet is dissolved in less than 60 minutes in conventional dissolution media. In some embodiments, more than about 40% of the tablet is dissolved in less than 60 minutes in conventional dissolution media. In some embodiments, more than about 50% of the tablet is dissolved in less than 60 minutes in conventional dissolution media. In some embodiments, more than about 60% of the tablet is dissolved in less than 60 minutes in conventional dissolution media. In some embodiments, more than about 70% of the tablet is dissolved in less than 60 minutes in conventional dissolution media. In some embodiments, more than about 80% of the tablet is dissolved in less than 60 minutes in conventional dissolution media. In some embodiments, more than about 90% of the tablet is dissolved in less than 60 minutes in conventional dissolution media. In some embodiments, more than about 100% of the tablet is dissolved in less than 60 minutes in conventional dissolution media.

In some embodiments, the tablet is produced at a commercial scale.

In some embodiments, the tablet comprises one or more pharmaceutically acceptable excipients.

In some embodiments, the tablet is coated with a coating material, e.g., a sealant. In some embodiments, the coating material is water soluble. In some embodiments, the coating material comprises a polymer, plasticizer, a pigment, or any combination thereof. In some embodiments, the coating material is in the form of a film coating, e.g., a glossy film, a pH independent film coating, an aqueous film coating, a dry powder film coating (e.g., complete dry powder film coating), or any combination thereof. In some embodiments, the coating material is highly adhesive. In some embodiments, the coating material provides low level of water permeation. In some embodiments, the coating material provides oxygen barrier protection. In some embodiments, the coating material allows immediate disintegration for fast release of a compound or pharmaceutically acceptable salt described herein. In some embodiments, the coating material is pigmented, clear, or white. In some embodiments, the coating is an enteric coating. Exemplary coating materials include, without limitation, polyvinylpyrrolidone, polyvinyl alcohol, an acrylate-methacrylic acid copolymer, a methacrylate-methacrylic acid copolymer, cellulose acetate phthalate, cellulose acetate succinate, hydroxypropyl methylcellulose phthalate, hydroxypropyl methylcellulose acetate succinate, polyvinyl acetate phthalate, shellac, cellulose acetate trimellitate, sodium alginate, zein, and any combinations thereof.

Pharmaceutically Acceptable Excipients

In some embodiments, the pharmaceutical composition comprises a pharmaceutically acceptable excipient. In some embodiments, the composition is free of pharmaceutically acceptable excipients. The term "pharmaceutically acceptable excipient", as used herein, means one or more compatible solid or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. In some embodiments, the pharmaceutically acceptable excipient is of sufficiently high purity and sufficiently low toxicity to render them suitable for administration preferably to an animal, preferably mammal, being treated.

Some examples of substances, which can serve as pharmaceutically acceptable excipients include:

Amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, the amino acid is arginine. In some embodiments, the amino acid is L-arginine.

Monosaccharides such as glucose (dextrose), arabinose, mannitol, fructose (levulose), and galactose.

Cellulose and its derivatives such as sodium carboxymethyl cellulose, ethyl cellulose, and methyl cellulose.

Solid lubricants such as talc, stearic acid, magnesium stearate, and sodium stearyl fumarate.

Polyols such as propylene glycol, glycerin, sorbitol, mannitol, and polyethylene glycol.

Emulsifiers such as the polysorbates.

Wetting agents such as sodium lauryl sulfate, Tween*, Span, alkyl sulphates, and alkyl ethoxylate sulphates.

Diluents such as calcium carbonate, microcrystalline cellulose, calcium phosphate, starch, pregelatinized starch, sodium carbonate, mannitol, and lactose.

Binders such as starches (corn starch and potato starch), gelatin, sucrose, hydroxypropyl cellulose (HPC), polyvinylpyrrolidone (PVP), and hydroxypropyl methyl cellulose (HPMC).

Disintegrants such as starch, and alginic acid.

Super-disintegrants such as ac-di-sol, croscarmellose sodium, sodium starch glycolate and crospovidone.

Glidants such as silicon dioxide.

Coloring agents such as the FD&C dyes.

Sweeteners and flavoring agents, such as aspartame, saccharin, menthol, peppermint, and fruit flavors.

Preservatives such as benzalkonium chloride, PHMB, chlorobutanol, thimerosal, phenylmercuric, acetate, phenylmercuric nitrate, parabens, and sodium benzoate.

Tonicity adjustors such as sodium chloride, potassium chloride, mannitol, and glycerin.

Antioxidants such as sodium bisulfite, acetone sodium bisulfite, sodium formaldehyde, sulfoxylate, thiourea, and EDTA.

pH adjuster such as NaOH, sodium carbonate, sodium acetate, HCl, and citric acid.

Cryoprotectants such as sodium or potassium phosphates, citric acid, tartaric acid, gelatin, and carbohydrates such as dextrose, mannitol, and dextran.

Cationic surfactants such as cetrimide, benzalkonium chloride and cetylpyridinium chloride.

Anion surfactants such as alkyl sulphates, alkyl ethoxylate sulphates, soaps, carboxylates, sulfates, and sulfonates.

Non-ionic surfactants such as polyoxyethylene derivatives, polyoxypropylene derivatives, polyol derivatives, polyol esters, polyoxyethylene esters, poloxamers, glyol esters, glycerol esters, sorbitan derivatives, polyethylene glycol (PEG-40, PEG-50, PEG-55), and ethers of fatty alcohols.

Organic materials such as carbohydrate and modified carbohydrates, lactose, α-lactose monohydrate, spray dried lactose and anhydrous lactose, starch and pregelatinized starch, sucrose, manitol, sorbitol, cellulose, powdered cellulose and microcrystalline cellulose.

Inorganic materials such as calcium phosphates (anhydrous dibasic calcium phosphate, dibasic calcium phosphate and tribasic calcium phosphate).

Co-processed diluents.

Surfactants such as sodium lauryl sulfate.

Compression aids.

Anti-tacking agents such as silicon dioxide and talc

Amounts

In some embodiments, the pharmaceutical composition, in the form of a tablet or capsule, comprises between about 1 mg and about 500 mg of a compound or pharmaceutically acceptable salt described herein. In some embodiments, the pharmaceutical composition, in the form of a tablet or capsule, comprises between about 1 mg and about 400 mg of a compound or pharmaceutically acceptable salt described herein. In some embodiments, the pharmaceutical composition, in the form of a tablet or capsule, comprises between about 1 mg and about 300 mg of a compound or pharmaceutically acceptable salt described herein. In some embodiments, the pharmaceutical composition, in the form of a tablet or capsule, comprises between about 1 mg and about 200 mg of a compound or pharmaceutically acceptable salt described herein. In some embodiments, the pharmaceutical composition, in the form of a tablet or capsule, comprises between about 1 mg and about 100 mg of a compound or pharmaceutically acceptable salt described herein. In some embodiments, the pharmaceutical composition, in the form of a tablet or capsule, comprises between about 1 mg and about 90 mg of a compound or pharmaceutically acceptable salt described herein. In some embodiments, the pharmaceutical composition, in the form of a tablet or capsule, comprises between about 1 mg and about 80 mg of a compound or pharmaceutically acceptable salt described herein. In some embodiments, the pharmaceutical composition, in the form of a tablet or capsule, comprises between about 1 mg and about 70 mg of a compound or pharmaceutically acceptable salt described herein. In some embodiments, the pharmaceutical composition, in the form of a tablet or capsule, comprises between about 1 mg and about 60 mg of a compound or pharmaceutically acceptable salt described herein. In some embodiments, the pharmaceutical composition, in the form of a tablet or capsule, comprises between about 1 mg and about 50 mg of a compound or pharmaceutically acceptable salt described herein. In some embodiments, the pharmaceutical composition, in the form of a tablet or capsule, comprises between about 1 mg and about 40 mg of a compound or pharmaceutically acceptable salt described herein. In some embodiments, the pharmaceutical composition, in the form of a tablet or capsule, comprises between about 1 mg and about 30 mg of a compound or pharmaceutically acceptable salt described herein. In some embodiments, the pharmaceutical composition, in the form of a tablet or capsule, comprises between about 1 mg and about 20 mg of a compound or pharmaceutically acceptable salt described herein. In some embodiments, the pharmaceutical composition, in the form of a tablet or capsule, comprises between about 1 mg and about 10 mg of a compound or pharmaceutically acceptable salt described herein.

In some embodiments, the pharmaceutical composition, in the form of a tablet or capsule, comprises between about 10 mg and about 500 mg of a compound or pharmaceutically acceptable salt described herein. In some embodiments, the pharmaceutical composition, in the form of a tablet or capsule, comprises between about 10 mg and about 400 mg of a compound or pharmaceutically acceptable salt described herein. In some embodiments, the pharmaceutical composition, in the form of a tablet or capsule, comprises between about 10 mg and about 300 mg of a compound or pharmaceutically acceptable salt described herein. In some embodiments, the pharmaceutical composition, in the form of a tablet or capsule, comprises between about 10 mg and about 200 mg of a compound or pharmaceutically acceptable salt described herein. In some embodiments, the pharmaceutical composition, in the form of a tablet or capsule, comprises between about 10 mg and about 100 mg of a compound or pharmaceutically acceptable salt described herein. In some embodiments, the pharmaceutical composition, in the form of a tablet or capsule, comprises between about 10 mg and about 90 mg of a compound or pharmaceutically acceptable salt described herein. In some embodiments, the pharmaceutical composition, in the form of a tablet or capsule, comprises between about 10 mg and about 80 mg of a compound or pharmaceutically acceptable salt described herein. In some embodiments, the pharmaceutical composition, in the form of a tablet or capsule, comprises between about 10 mg and about 70 mg of a compound or pharmaceutically acceptable salt described herein. In some embodiments, the pharmaceutical composition, in the form of a tablet or capsule, comprises between about 10 mg and about 60 mg of a compound or pharmaceutically acceptable salt described herein f. In some embodiments, the pharmaceutical composition, in the form of a tablet or capsule, comprises between about 10 mg and about 50 mg of a compound or pharmaceutically acceptable salt described herein. In some embodiments, the pharmaceutical composition, in the form of a tablet or capsule, comprises between about 10 mg and about 40 mg of a compound or pharmaceutically acceptable salt described herein. In some embodiments, the pharmaceutical composition, in the form of a tablet or capsule, comprises between about 10 mg and about 30 mg of a compound or pharmaceutically acceptable salt described herein. In some embodiments, the pharmaceutical composition, in the form of a tablet or capsule, comprises between about 10 mg and about 20 mg of a compound or pharmaceutically acceptable salt described herein.

Particle Size

In some embodiments, the pharmaceutical composition, in the form of a tablet or a capsule, comprises a compound or pharmaceutically acceptable salt described herein, in the form of microparticles. In some embodiments, the microparticles have an average size from about 1 μm to about 100 μm. In some embodiments, the microparticles have an average size from about 1 μm to about 50 μm. In some embodiments, the microparticles have an average size from about 1 μm to about 30 μm. In some embodiments, the microparticles have an average size from about 1 μm to about 20 μm. In some embodiments, the microparticles have an average size from about 5 μm to about 15 μm. In some embodiments, the microparticles have an average size from about 1 μm to about 10 μm. In some embodiments, the microparticles have an average size from about 3 μm to about 10 μm. In some embodiments, the microparticles have an average size from about 4 μm to about 9 μm.

Methods of Treatment

Disclosed herein are methods of treating polycystic ovary syndrome (PCOS) in a subject in need thereof, comprising administering a compound or pharmaceutically acceptable salt described herein. In some embodiments, the subject in need thereof has PCOS-FAH. In some embodiments, the subject in need thereof has PCOS–FOH+FAH. In some embodiments, the methods described herein result in the reduction of a level of a hormone. Such hormones include deoxycorticosterone, 11-deoxycortisol, cortisol, corticosterone, pregnenolone, 17α-hydroxy pregnenolone, progesterone, 17-OHP, dehydroepiandrosterone (DHEA), dehydroepiandrosterone-sulfate (DHEAS), androstenediol, androstenedione (A4), testosterone (T), dihydrotestosterone (DHT), estrone, estradiol, estriol, 11β-hydroxyandrostenedione (11OHA4), 11β-hydroxytestosterone (11OHT), 11-ketoandrostenedione (11KA4), 11-ketotestosterone (11KT), 11β-hydroxy-5α-androstenedione (11OHDHA4), 11-keto-5α-androstenedione (11KDHA4), 11β-hydroxydihydrotestosterone (11OHDHT), 11-ketodihydrotestosterone (11KDHT) and ACTH. In some embodiments, the methods described herein result in the reduction of 17-OHP levels. In some embodiments, the methods described herein result in the reduction of A4 levels. In some embodiments, the methods described herein result in the reduction of ACTH levels. In some embodiments, the methods described herein result in the reduction of DHEA levels. In some embodiments, the methods described herein result in the reduction of DHEAS levels. In some embodiments, the methods described herein result in the reduction of testosterone (T) levels. In some embodiments, the methods described herein result in the reduction of DHT levels. In some embodiments, the methods described herein result in the reduction of 11OHA4 levels. In some embodiments, the methods described herein result in the reduction of 11OHT levels. In some embodiments, the methods described herein result in the reduction of 11KA4 levels. In some embodiments, the methods described herein result in the reduction of 11KT levels.

Further, in some embodiments, the methods described herein result in the maintenance of the reduction of 17-OHP, A4, ACTH, DHEA, DHEAS, T, DHT, 11OHA4, 11OHT, 11KA4, and/or 11KT levels. In some embodiments, the reductions of 17-OHP, A4, ACTH, DHEA, DHEAS, T, DHT, 11OHA4, 11OHT, 11KA4 and/or 11KT levels may last for at least 24 hours, 36 hours, 48 hours, 60 hours, 72 hours, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 2 years, 5 years, 10 years, 15 years, 20 years, 25 years, 30 years, 35 years, 40 years, 45 years, 50 years, 55 years, 60 years, 65 years, 70 years, 75 years, 80 years, 85 years, 90 years, 95 years, or 100 years.

In some embodiments, the methods described herein result in the reduction of DHEAS levels. In some embodiments, the DHEAS level is reduced by at least about 1%, 2%, 5%, 10%, 15%, 20%, 25%, 30%, 35%, 40%, 45%, 50%, 55%, 60%, 65%, 70%, 75%, 80%, 85%, 90%, or 95% from baseline. The baseline level of the DHEAS may be measured in a subject before beginning the treatment disclosed herein. In some embodiments, the DHEAS level is reduced by at least 5% from baseline. In some embodiments, the reduced DHEAS level from baseline may be maintained for at least about 1 hour, 2 hours, 4 hours, 8 hours, 12 hours, 24 hours, 48 hours, 1 week, 2 weeks, 3 weeks, 4 weeks, 5 weeks, 6 weeks, 7 weeks, 8 weeks, 9 weeks, 10 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, or 30 weeks.

Further, in some embodiments, the methods described herein result in the maintenance of the reduction of 17-OHP, A4, ACTH, T, DHT, 11OHA4, 11OHT, 11KA4 and/or 11KT levels. In some embodiments, the reductions of 17-OHP, A4, ACTH T, DHT, 11OHA4, 11OHT, 11KA4 and/or 11KT levels may last for at least 24 hours, 36 hours, 48 hours, 60 hours, 72 hours, 4 days, 5 days, 6 days, 7 days, 8 days, 9 days, 10 days, 11 days, 12 days, 13 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, 2 years, 5 years, 10 years, 15 years, 20 years, 25 years, 30 years, 35 years, 40 years, 45 years, 50 years, 55 years, 60 years, 65 years, 70 years, 75 years, 80 years, 85 years, 90 years, 95 years, or 100 years.

In some embodiments, disclosed herein are methods for treating PCOS in a subject in need thereof, and the methods further comprise accessing a source of excessive androgen; and administering a $CRF_1$ antagonist or pharmaceutically acceptable salt thereof. In some embodiments, accessing a source of excessive androgen comprises measuring the primary source of excessive androgen produced in the subject suffering PCOS. In some embodiments, the primary source is the ovaries. In some embodiments, the primary source is the adrenal glands. In some embodiments, the primary source is both the ovaries and the adrenal glands. In some embodiments, the primary source is an organ that is able to produce androgen.

In some embodiments, cosyntropin or any other suitable hormones or chemical compounds may be administered to a subject for ACTH response in order to test for adrenal hyperandrogenism. In some embodiments, the cosyntropin is administered at a dose at least about 0.25, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 200, 250 or μg/m². In some embodiments, the cosyntropin is administered at a dose at about the range between the doses disclosed herein. In some embodiments, the cosyntropin is administered at a dose at most about 250, 200, 100, 95, 90, 85, 80, 75, 70, 65, 60, 55, 50, 45, 40, 35, 30, 25, 20, 15, 10, 5, 4, 3, 2, 1 μg/m².

In some embodiments, the subject will be treated for a period of about 1 week to about 40 weeks. In some embodiments, the subject will be treated for a period of about 2 weeks to about 39 weeks. In some embodiments, the subject will be treated for a period of about 3 weeks to about 38 weeks. In some embodiments, the subject will be treated for a period of about 4 weeks to about 36 weeks. In some embodiments, the subject will be treated for a period of about 1 month to 12 months. In some embodiments, the subject will be treated for a period of about 10 months to 10 years. In some embodiments, the subject will be treated for a period of about 1 months to 10 years. In some embodiments, the subject will be treated for a period of about 10 months to 20 years. In some embodiments, the subject will be treated for a period of about 1 months to 20 years. In some embodiments, the subject will be treated for a period of about 10 months to 30 years. In some embodiments, the subject will be treated for a period of about 1 months to 30 years. In some embodiments, the subject will be treated for a period of about 10 months to 40 years. In some embodiments, the subject will be treated for a period of about 1 months to 40 years. In some embodiments, the subject will be treated for a period of about 10 months to 50 years. In some embodiments, the subject will be treated for a period of about 1 months to 50 years.

In some embodiments, the $CRF_1$ antagonist or pharmaceutically acceptable salt thereof is selected from the group consisting of: Antalarmin hydrochloride, CP-154,526, CP-376395 hydrochloride, NBI 27914 hydrochloride, NBI 35965 hydrochloride, NGD 98-2 hydrochloride, Pexacerfont, R 121919 hydrochloride, SSR125543 (crinecerfont), AND SN003.

In some embodiments, the $CRF_1$ antagonist is a compound of Formula (I):

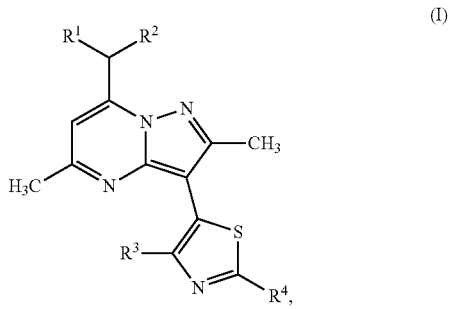

or a pharmaceutically acceptable salt thereof, wherein:
$R^1$ and $R^2$ are independently ethyl or n-propyl;
$R^3$ is hydrogen, F, Cl, Br, methyl, trifluoromethyl, or methoxy; and
$R^4$ is hydrogen, Br, —$NR^aR^b$, methoxymethyl, n-butyl, acetamido, pyridin-4-yl, morpholin-4-yl,

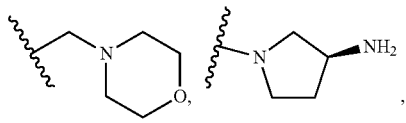

-continued

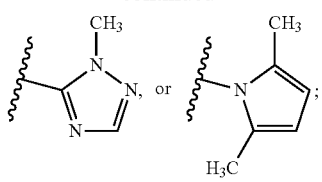

and $R^a$ and $R^b$ are independently hydrogen, $C_1$-$C_3$alkyl, —CH$_2$CH$_2$NH$_2$, —CH$_2$CH$_2$NHC(O)OC(CH$_3$)$_3$— CH$_2$CH$_2$NHC(O)OC(CH$_3$)$_3$, or —CH$_2$CH$_2$NHCH$_2$CH$_2$CH$_3$—.

In some embodiments, $R^3$ is F, Cl, Br, methyl, or trifluoromethyl. In some embodiments, $R^3$ is Cl, Br, or methyl.

In some embodiments, $R^4$ is Br, —NR$^a$R$^b$—NR$^a$R$^b$, pyridin-4-yl, morpholin-4-yl, or

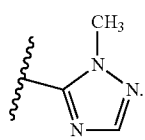

In some embodiments, $R^4$ is morpholin-4-yl or

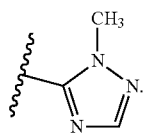

In some embodiments, $R^4$ is hydrogen, Br, —NR$^a$R$^b$ and $R^a$ and $R^b$ are independently $C_1$-$C_3$alkyl.

In some embodiments, the compound is

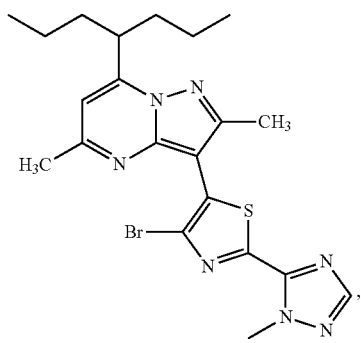 [SMILES: CCCC(CCC)c1cc(C)nc2c(-c3sc(-c4ncnn4C)nc3Br)c(C)nn12 ; ","]

or a pharmaceutically acceptable salt thereof.

In some embodiments, the compound is

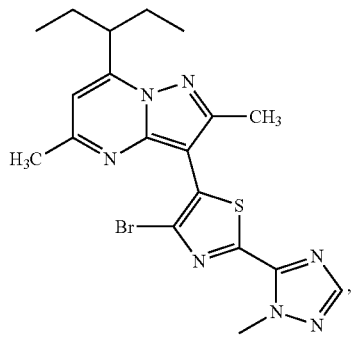 [SMILES: CCC(CC)c1cc(C)nc2c(-c3sc(-c4ncnn4C)nc3Br)c(C)nn12 ; ","]

or a pharmaceutically acceptable salt thereof.

In some embodiments, the compound is

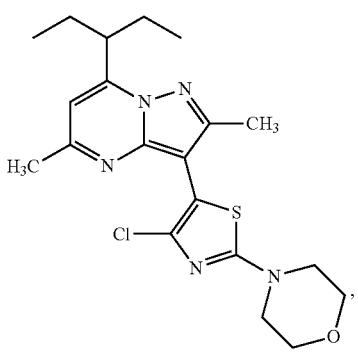 [SMILES: CCC(CC)c1cc(C)nc2c(-c3sc(N4CCOCC4)nc3Cl)c(C)nn12 ; ","]

or a pharmaceutically acceptable salt thereof.

In some embodiments, the CRF$_1$ antagonist or pharmaceutically acceptable salt is administered in a dose of about 10 mg to about 200 mg total daily dose to the subject. In some embodiments, the CRF$_1$ antagonist or pharmaceutically acceptable salt is administered in a dose of about 200 mg total daily dose to the subject.

In some embodiments, the CRF$_1$ antagonist or pharmaceutically acceptable salt is administered in a dose of about 150 mg total daily dose to the subject. In some embodiments, the CRF$_1$ antagonist or pharmaceutically acceptable salt is administered in a dose of about 100 mg total daily dose to the subject. In some embodiments, the CRF$_1$ antagonist or pharmaceutically acceptable salt is administered in a dose of about 50 mg total daily dose to the subject. In some embodiments, the CRF$_1$ antagonist or pharmaceutically acceptable salt is administered in a dose of about 40 mg total daily dose to the subject. In some embodiments, the CRF$_1$ antagonist or pharmaceutically acceptable salt is administered in a dose of about 30 mg total daily dose to the subject. In some embodiments, the CRF$_1$ antagonist or pharmaceutically acceptable salt is administered in a dose of about 25 mg total daily dose to the subject. In some embodiments, the CRF$_1$ antagonist or pharmaceutically acceptable salt is administered in a dose of about 20 mg total daily dose to the subject. In some embodiments, the CRF$_1$ antagonist or pharmaceutically acceptable salt is administered in a dose of about 15 mg total daily dose to the subject. In some embodiments, the CRF$_1$ antagonist or pharmaceutically acceptable salt is administered in a dose of about 10 mg total daily dose to the subject. In some embodiments, the CRF$_1$ antagonist or pharmaceutically acceptable salt is administered in a dose of about 5 mg total daily dose to the subject.

In some embodiments, the $CRF_1$ antagonist or pharmaceutically acceptable salt is in the form of microparticles. In some embodiments, the average size of the microparticles is between about 1 µm to about 20 µm. In some embodiments, the average size of the microparticles is between about 5 µm to about 15 µm. In some embodiments, the average size of the microparticles is less than about 10µ.

In some embodiments, the $CRF_1$ antagonist or pharmaceutically acceptable salt thereof is administered as a pharmaceutical composition. In some embodiments, the steroid or a pharmaceutically acceptable salt thereof is administered as a pharmaceutical composition.

In some embodiments, the pharmaceutical composition is in the form of a capsule or a tablet. In some embodiments, the capsule is a hard gelatin capsule. In some embodiments, the capsule is a soft gelatin capsule. In some embodiments, the capsule is formed using materials selected from the group consisting of natural gelatin, synthetic gelatin, pectin, casein, collagen, protein, modified starch, polyvinylpyrrolidone, acrylic polymers, cellulose derivatives, and any combinations thereof.

In some embodiments, the pharmaceutical composition is free of additional excipients. In some embodiments, the pharmaceutical composition further comprises one or more pharmaceutically acceptable excipients. In some embodiments, the pharmaceutical composition is in the form of a tablet. In some embodiments, the pharmaceutical composition further comprises one or more pharmaceutically acceptable excipients.

In some embodiments, $CRF_1$ antagonist or pharmaceutically acceptable salt is formulated as a capsule or a tablet as to provide a Tmax of about 1 to about 8 hours in a subject. In some embodiments, $CRF_1$ antagonist or pharmaceutically acceptable salt is formulated as a capsule or a tablet as to provide a Tmax of about 2 to about 7 hours in a subject. In some embodiments, $CRF_1$ antagonist or pharmaceutically acceptable salt is formulated as a capsule or a tablet as to provide a Tmax of about 2 to about 6 hours in a subject. In some embodiments, $CRF_1$ antagonist or pharmaceutically acceptable salt is formulated as a capsule or a tablet as to provide a Tmax of about 3 to about 5 hours in a subject.

In some embodiments, $CRF_1$ antagonist or pharmaceutically acceptable salt is formulated as a capsule or a tablet as to provide a Tmax of about 8 hours in a subject. In some embodiments, $CRF_1$ antagonist or pharmaceutically acceptable salt is formulated as a capsule or a tablet as to provide a Tmax of about 7 hours in a subject. In some embodiments, $CRF_1$ antagonist or pharmaceutically acceptable salt is formulated as a capsule or a tablet as to provide a Tmax of about 6 hours in a subject. In some embodiments, $CRF_1$ antagonist or pharmaceutically acceptable salt is formulated as a capsule or a tablet as to provide a Tmax of about 5 hours in a subject. In some embodiments, $CRF_1$ antagonist or pharmaceutically acceptable salt is formulated as a capsule or a tablet as to provide a Tmax of about 4 hours in a subject. In some embodiments, $CRF_1$ antagonist or pharmaceutically acceptable salt is formulated as a capsule or a tablet as to provide a Tmax of about 3 hours in a subject. In some embodiments, $CRF_1$ antagonist or pharmaceutically acceptable salt is formulated as a capsule or a tablet as to provide a Tmax of about 2 hours in a subject. In some embodiments, $CRF_1$ antagonist or pharmaceutically acceptable salt is formulated as a capsule or a tablet as to provide a Tmax of about 1 hour in a subject.

In some embodiments, the methods described herein include administration of the pharmaceutical composition comprising $CRF_1$ antagonist or pharmaceutically acceptable salt, or a pharmaceutically acceptable salt or solvate thereof once a month, twice a month, three times a month, once a week, twice a week, three times a week, once every two days, once a day, twice a day, three times a day, or four times a day. In some embodiments, the methods described herein administer $CRF_1$ antagonist or pharmaceutically acceptable salt, or a pharmaceutically acceptable salt or solvate thereof once a day. In some embodiments, the methods described herein administer $CRF_1$ antagonist or pharmaceutically acceptable salt, or a pharmaceutically acceptable salt or solvate thereof twice a day.

In some embodiments, the methods described herein include administration of about 1 mg to about 2000 mg of $CRF_1$ antagonist or pharmaceutically acceptable salt, or a pharmaceutically acceptable salt or solvate thereof, per day. In some embodiments, $CRF_1$ antagonist or pharmaceutically acceptable salt is administered at a dose between about 50 mg/day and about 1600 mg/day. In some embodiments, Compound 3 is administered at a dose between about 50 mg/day and about 1500 mg/day. In some embodiments, Compound 3 is administered at a dose between about 50 mg/day and about 1400 mg/day. In some embodiments, Compound 3 is administered at a dose between about 50 mg/day and about 1300 mg/day. In some embodiments, Compound 3 is administered at a dose between about 50 mg/day and about 1200 mg/day. In some embodiments, Compound 3 is administered at a dose between about 50 mg/day and about 1100 mg/day. In some embodiments, Compound 3 is administered at a dose between about 50 mg/day and about 1000 mg/day. In some embodiments, Compound 3 is administered at a dose between about 50 mg/day and about 900 mg/day. In some embodiments, Compound 3 is administered at a dose between about 50 mg/day and about 800 mg/day. In some embodiments, Compound 3 is administered at a dose between about 60 mg/day and about 800 mg/day. In some embodiments, Compound 3 is administered at a dose between about 70 mg/day and about 800 mg/day. In some embodiments, Compound 3 is administered at a dose between about 80 mg/day and about 800 mg/day. In some embodiments, Compound 3 is administered at a dose between about 90 mg/day and about 800 mg/day. In some embodiments, Compound 3 is administered at a dose between about 100 mg/day and about 800 mg/day. In some embodiments, Compound 3 is administered at a dose between about 100 mg/day and about 700 mg/day. In some embodiments, Compound 3 is administered at a dose between about 100 mg/day and about 600 mg/day. In some embodiments, Compound 3 is administered at a dose between 150 mg/day and about 600 mg/day. In some embodiments, Compound 3 is administered at a dose between 200 mg/day and about 600 mg/day. In some embodiments, Compound 3 is administered at a dose between 200 mg/day and about 500 mg/day. In some embodiments, Compound 3 is administered at a dose between 200 mg/day and about 400 mg/day. In some embodiments, Compound 3 is administered at a dose between 25 mg/day and about 200 mg/day.

In some embodiments, Compound 3 is administered at a dose of about 500 mg/day. In some embodiments, Compound 3 is administered at a dose of about 400 mg/day. In some embodiments, Compound 3 is administered at a dose of about 300 mg/day. In some embodiments, Compound 3 is administered at a dose of about 200 mg/day. In some embodiments, Compound 3 is administered at a dose of about 150 mg/day. In some embodiments, Compound 3 is administered at a dose of about 100 mg/day. In some embodiments, Compound 3 is administered at a dose of about 50 mg/day.

In some embodiments, about 50 mg to about 1600 mg of $CRF_1$ antagonist or pharmaceutically acceptable salt, or a pharmaceutically acceptable salt or solvate thereof, is administered per day. In some embodiments, about 100 mg to about 1600 mg of $CRF_1$ antagonist or pharmaceutically acceptable salt, or a pharmaceutically acceptable salt or solvate thereof, is administered per day. In some embodiments, about 200 mg to about 1600 mg of $CRF_1$ antagonist or pharmaceutically acceptable salt, or a pharmaceutically acceptable salt or solvate thereof, is administered per day. In some embodiments, about 200 mg to about 1200 mg of $CRF_1$ antagonist or pharmaceutically acceptable salt, or a pharmaceutically acceptable salt or solvate thereof, is administered per day. In some embodiments, about 200 mg to about 1000 mg of $CRF_1$ antagonist or pharmaceutically acceptable salt, or a pharmaceutically acceptable salt or solvate thereof, is administered per day. In some embodiments, about 200 mg to about 800 mg of $CRF_1$ antagonist or pharmaceutically acceptable salt, or a pharmaceutically acceptable salt or solvate thereof, is administered per day. In some embodiments, about 100 mg to about 800 mg of $CRF_1$ antagonist or pharmaceutically acceptable salt, or a pharmaceutically acceptable salt or solvate thereof, is administered per day. In some embodiments, about 200 mg to about 800 mg of $CRF_1$ antagonist or pharmaceutically acceptable salt, or a pharmaceutically acceptable salt or solvate thereof, is administered per day. In some embodiments, about 100 mg to about 600 mg of $CRF_1$ antagonist or pharmaceutically acceptable salt, or a pharmaceutically acceptable salt or solvate thereof, is administered per day. In some embodiments, about 200 mg to about 600 mg of $CRF_1$ antagonist or pharmaceutically acceptable salt is administered per day. In some embodiments, about 300 mg to about 600 mg of $CRF_1$ antagonist or pharmaceutically acceptable salt, or a pharmaceutically acceptable salt or solvate thereof, is administered per day. In some embodiments, about 100 mg to about 400 mg of $CRF_1$ antagonist or pharmaceutically acceptable salt, or a pharmaceutically acceptable salt or solvate thereof, is administered per day. In some embodiments, about 200 mg to about 400 mg of $CRF_1$ antagonist or pharmaceutically acceptable salt, or a pharmaceutically acceptable salt or solvate thereof, is administered per day. In some embodiments, about 300 mg to about 400 mg of $CRF_1$ antagonist or pharmaceutically acceptable salt, or a pharmaceutically acceptable salt or solvate thereof, is administered each day.

In some embodiments, less than about 2000 mg $CRF_1$ antagonist or pharmaceutically acceptable salt, or a pharmaceutically acceptable salt or solvate thereof, is administered per day. In some embodiments, less than about 1800 mg $CRF_1$ antagonist or pharmaceutically acceptable salt, or a pharmaceutically acceptable salt or solvate thereof, is administered per day. In some embodiments, less than about 1600 mg $CRF_1$ antagonist or pharmaceutically acceptable salt, or a pharmaceutically acceptable salt or solvate thereof, is administered per day. In some embodiments, less than about 1400 mg $CRF_1$ antagonist or pharmaceutically acceptable salt, or a pharmaceutically acceptable salt or solvate thereof, is administered per day. In some embodiments, less than about 1200 mg $CRF_1$ antagonist or pharmaceutically acceptable salt, or a pharmaceutically acceptable salt or solvate thereof, is administered per day. In some embodiments, less than about 1000 mg $CRF_1$ antagonist or pharmaceutically acceptable salt, or a pharmaceutically acceptable salt or solvate thereof, is administered per day. In some embodiments, less than about 800 mg $CRF_1$ antagonist or pharmaceutically acceptable salt, or a pharmaceutically acceptable salt or solvate thereof, is administered per day. In some embodiments, less than about 600 mg $CRF_1$ antagonist or pharmaceutically acceptable salt, or a pharmaceutically acceptable salt or solvate thereof, is administered per day. In some embodiments, less than about 500 mg $CRF_1$ antagonist or pharmaceutically acceptable salt, or a pharmaceutically acceptable salt or solvate thereof, is administered per day. In some embodiments, less than about 400 mg $CRF_1$ antagonist or pharmaceutically acceptable salt, or a pharmaceutically acceptable salt or solvate thereof, is administered per day. In some embodiments, less than about 300 mg $CRF_1$ antagonist or pharmaceutically acceptable salt, or a pharmaceutically acceptable salt or solvate thereof, is administered per day. In some embodiments, less than about 200 mg $CRF_1$ antagonist or pharmaceutically acceptable salt, or a pharmaceutically acceptable salt or solvate thereof, is administered per day.

In some embodiments, the methods described herein include administration of the pharmaceutical compositions described herein wherein the subject is in the fed state. In some embodiments, the methods described herein include administration of the pharmaceutical compositions described herein wherein the subject is in the fasted state.

In some embodiments, the methods described herein include administration of the pharmaceutical compositions described herein at bedtime.

In some embodiments, the methods described herein include administration of the pharmaceutical compositions described herein less than about 4 hours before sleep. In some embodiments, the methods described herein include administration of the pharmaceutical compositions described herein less than about 3 hours before sleep. In some embodiments, the methods described herein include administration of the pharmaceutical compositions described herein less than about 2 hours before sleep. In some embodiments, the methods described herein include administration of the pharmaceutical compositions described herein less than about 1 hour before sleep. In some embodiments, the methods described herein include administration of the pharmaceutical compositions described herein less than about 30 mins before sleep.

In some embodiments, the methods described herein include administration of the pharmaceutical compositions described herein in the evening.

In some embodiments, the methods described herein include administration of the pharmaceutical compositions described herein at about 11 μm at night. In some embodiments, the methods described herein include administration of the pharmaceutical compositions described herein at about 10 μm at night. In some embodiments, the methods described herein include administration of the pharmaceutical compositions described herein at about 9 μm at night. In some embodiments, the methods described herein include administration of the pharmaceutical compositions described herein at about 8 μm at night.

In some embodiments, the methods described herein include administration of the pharmaceutical compositions described herein in combination with eflornithine and/or retinoids.

In some embodiments, the methods described herein include administration of the pharmaceutical compositions described herein in combination with contraceptive pills containing androgen receptor blockers such as cyproterone acetate, spironolactone, flutamide, or 5α-reductase inhibitors.

In some embodiments, the levels of DHEA, DHEAS, A4, 11OHA4, T, 11OHT, DHT and/or ACTH in the subject are determined from a biological sample from the subject. In some embodiments, the biological sample is selected from the group of blood, blood fractions, plasma, serum, urine, other types of bodily secretions, and saliva. In some embodiments, the biological sample is obtained non-invasively.

In some embodiments, the subject is a pediatric patient. In some embodiments, the subject is an adolescent. In some embodiments, the subject is from about 8 years old to about 18 years old. In some embodiments, the subject is an adult patient. In some embodiments, the subject is from about 18 years old to about 55 years old. In some embodiments, the subject is from about 18 years old to about 50 years old.

In some embodiments, the steroid and the $CRF_1$ antagonist are administered concurrently. In some embodiments, the steroid and the $CRF_1$ antagonist are administered in one pharmaceutical composition. In some embodiments, the steroid and the $CRF_1$ antagonist are administered concurrently in separate pharmaceutical compositions. In some embodiments, the steroid and the $CRF_1$ antagonist are administered sequentially.

EXAMPLES

The following examples further illustrate the invention but should not be construed as in any way limiting its scope. In particular, the processing conditions are merely exemplary and can be readily varied by one of ordinary skill in the art.

All methods described herein can be performed in a suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Unless defined otherwise, technical and scientific terms used herein have the same meaning as is commonly understood by one of skill in the art to which this invention belongs.

Example 1—Reduction of DHEAS Level in a Subject Who has Polycystic Ovary Syndrome (PCOS) and Elevated Adrenal Androgens Study Compound 3 in a double-blind, proof-of-concept study, evaluating the safety and efficacy of repeated doses of Compound 3 in adults with elevated adrenal androgens, PCOS-FAH or PCOS-FAH+FOH. After screening, eligible subjects with elevated adrenal androgens documented by elevated DHEAS will be randomized to either a compound 3 dose escalation arm or matching placebo arm.

The study is planned as a 3-period study with a duration of 4 weeks for Periods 1 and 2 and a duration of 8 weeks in Period 3 for a total treatment duration of 16 weeks. Subjects randomized to the compound 3 dose escalation arm will be treated with escalating doses of 50-mg, 100-mg or 200 mg based on achieving a DHEAS positive response criteria within each treatment period. Subjects not meeting the criteria will be dose escalated to the next highest dose in the preceding period. Subjects meeting the criteria will remain on their current dose level. Placebo subjects will remain on placebo through the full 16 weeks.

The population are composed of approximately 40 patients, who receive Compound 3 or matching placebo daily for up to 16 weeks. Compound 3 is administered as an oral daily dose. Patients are undergo PK/PD or PD only assessments, approximately every 2 weeks. A follow-up outpatient visit occurs 30 days after the last dose.

Study Design
  Study Type: Interventional
  Primary Purpose: Treatment
  Study Phase: Phase 2
  Interventional Study Model: Randomized
  Number of Arms: 2
  Masking: Masking of Study drug
  Allocation: Randomized (1:1)
  Enrollment: 40
Arms and Interventions:

| Arms | Assigned Intervention |
|---|---|
| Arm 1 | Drug: Compound 3 dose escalation (50, 100 and 200-mg) |
| Arm 2 | Drug: Matching Placebo |

Outcome Measures
Primary Outcome Measures:
  1. Safety and tolerability of Compound 3 in patients with elevated adrenal androgens (adverse effects, serious adverse effects, clinical laboratory parameters, etc.)
[Time Frame: 16 weeks]
Secondary Outcome Measures:
  2. Proportion of subjects with:
    a. ≥30% change from baseline in dehydroepiandrosterone sulfate (DHEAS)
    b. DHEAS<upper limit of normal (ULN)
    c. DHEAS<$75^{th}$ percentile of normal range (Q3)
[Time Fame: 4 to up to 16 weeks]
  3. Pharmacokinetics of compound 3
[Time Frame: 4 weeks]
Exploratory Outcome Measure:
  4. Changes in PD markers: Changes in cortisol, ACTH, DHEAS, DHEA, A4, T, 17-OHP, 11OHA4, 11OHT, 11KA4, 11KT
[Time Frame: up to 16 weeks]
Eligibility
  Minimum Age: 18 Years
  Maximum Age: 30 years
  Sex: Female only
  Gender Based: Yes
  Accepts Healthy Volunteers: No
  Criteria: Inclusion
Criteria:
Inclusion Criteria:
  Female subjects 18 to 30 years old, inclusive
  Subjects must have documented PCOS according to the NIH (1990) criteria
  BMI≤38 kg/m$^2$
  DHEAS level>age matched reference ULN at Screening
  Evidence of DHEA hyperresponsiveness to ACTH stimulation during Screening
Exclusion Criteria:
  Has a BMI>38 kg/m$^2$
  Has PCOS–FOH
  Has HbA1c>6.5% or Fasting plasma glucose>126 mg/dL
  Has a history that includes bilateral adrenalectomy or hypopituitarism
  Has a history of allergy or hypersensitivity to tildacerfont or any other $CRF_1$ receptor antagonist
  Clinically significant unstable medical condition, illness, or chronic disease
  Clinically significant uncontrolled psychiatric disorder Clinically significant abnormal laboratory finding or assessment
Pregnant or nursing females
Use of any other investigational drug within 30 days
Unable to understand and comply with the study procedures, understand the risks, and/or unwilling to provide written informed consent.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of treating polycystic ovary syndrome with functional ovarian hyperandrogenism and functional adrenal hyperandrogenism (PCOS–FOH+FAH) in a subject in need thereof, comprising administering a $CRF_1$ antagonist or pharmaceutically acceptable salt thereof,
wherein said $CRF_1$ antagonist is a compound of Formula (I):

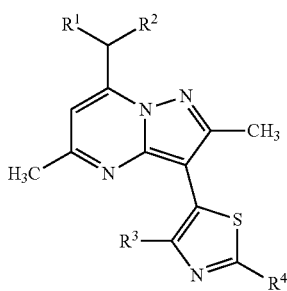

Formula (I)

or a pharmaceutically acceptable salt thereof, wherein:
$R^1$ and $R^2$ are independently ethyl or n-propyl;
$R^3$ is hydrogen, F, Cl, Br, methyl, trifluoromethyl, or methoxy;
$R^4$ is hydrogen, Br, —$NR^aR^b$, methoxymethyl, n-butyl, acetamido, pyridin-4-yl, morpholin-4-yl,

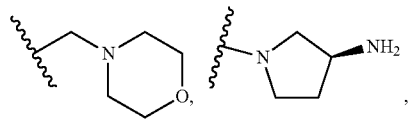

-continued

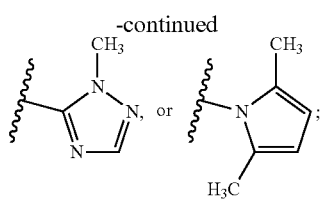

$R^a$ and $R^b$ are independently hydrogen, $C_1$-$C_3$alkyl, —$CH_2CH_2NH_2$, —$CH_2CH_2NHC(O)OC(CH_3)_3$, or —$CH_2CH_2NHCH_2CH_2CH_3$.

2. The method of claim 1, wherein the compound of Formula (I) is

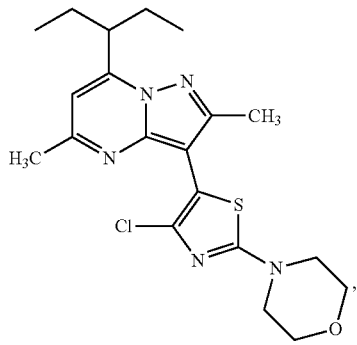 [SMILES: CCC(CC)c1cc(C)nc2c(-c3sc(N4CCOCC4)nc3Cl)c(C)nn12 ; ","]

or a pharmaceutically acceptable salt thereof.

3. The method of claim 1, wherein the $CRF_1$ antagonist or pharmaceutically acceptable salt is administered in a dose of about 5 mg to about 400 mg total daily dose to the subject.

4. The method of claim 1, wherein the $CRF_1$ antagonist or pharmaceutically acceptable salt is administered in a dose of about 300 mg total daily dose to the subject.

5. The method of claim 1, wherein the $CRF_1$ antagonist or pharmaceutically acceptable salt is administered in a dose of about 200 mg total daily dose to the subject.

6. The method of claim 1, wherein the $CRF_1$ antagonist or pharmaceutically acceptable salt is administered in a dose of about 150 mg total daily dose to the subject.

7. The method of claim 1, wherein the $CRF_1$ antagonist or pharmaceutically acceptable salt is administered in a dose of about 100 mg total daily dose to the subject.

8. The method of claim 1, wherein the $CRF_1$ antagonist or pharmaceutically acceptable salt is administered in a dose of about 75 mg total daily dose to the subject.

9. The method of claim 1, wherein the $CRF_1$ antagonist or pharmaceutically acceptable salt is administered in a dose of about 50 mg total daily dose to the subject.

10. The method of claim 1, wherein the $CRF_1$ antagonist or pharmaceutically acceptable salt is administered in a dose of about 25 mg total daily dose to the subject.

11. The method of claim 1, wherein the $CRF_1$ antagonist or pharmaceutically acceptable salt is administered in a dose of about 10 mg total daily dose to the subject.

12. The method of claim 1, wherein an adrenocorticotropic hormone (ACTH) level is reduced by at least 10% from baseline.

13. The method of claim 1, wherein a dehydroepiandrosterone sulfate (DHEAS) level is reduced from baseline.

14. The method of claim 1, wherein androstenedione (A4) level is reduced by at least 10% from baseline.

15. The method of claim 1, wherein 1β-hydroxyandrostenedione (11OHA4) level is reduced by at least 10% from baseline.

16. The method of claim 1, wherein 11β-hydroxytestosterone (11OHT) level is reduced by at least 10% from baseline.

17. The method of claim 14, wherein said reduced level from baseline is maintained for at least 24 hours.

18. The method of claim 2, wherein the compound of Formula (I) is administered at a dose between about 1 mg/day and about 200 mg/day.

19. The method of claim 1, wherein the pharmaceutical composition is in the form of microparticles.

20. The method of claim 1, wherein the pharmaceutical composition is in the form of a capsule or a tablet.

21. The method of claim 1, wherein the subject is a pediatric patient or an adult patient.

* * * * *